United States Patent
Portman

(10) Patent No.: US 11,253,569 B2
(45) Date of Patent: Feb. 22, 2022

(54) METHODS OF TREATING KAWASAKI DISEASE

(71) Applicant: Seattle Children's Hospital, Seattle, WA (US)

(72) Inventor: Michael A. Portman, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

(21) Appl. No.: 16/401,698

(22) Filed: May 2, 2019

(65) Prior Publication Data

US 2019/0336573 A1 Nov. 7, 2019

Related U.S. Application Data

(60) Provisional application No. 62/666,316, filed on May 3, 2018.

(51) Int. Cl.

| | | |
|---|---|---|
| A61K 38/17 | (2006.01) |
| A61P 17/00 | (2006.01) |
| C07K 16/06 | (2006.01) |
| C07K 16/24 | (2006.01) |
| A61K 39/395 | (2006.01) |
| A61K 31/047 | (2006.01) |
| A61K 31/7016 | (2006.01) |
| A61K 31/717 | (2006.01) |
| A61K 31/718 | (2006.01) |
| A61K 31/25 | (2006.01) |
| A61K 31/05 | (2006.01) |
| A61K 47/18 | (2017.01) |
| A61K 47/36 | (2006.01) |
| A61K 47/02 | (2006.01) |
| A61K 47/12 | (2006.01) |
| A61K 31/60 | (2006.01) |
| A61K 31/192 | (2006.01) |
| A61K 9/00 | (2006.01) |

(52) U.S. Cl.
CPC ........ *A61K 38/1709* (2013.01); *A61K 9/0019* (2013.01); *A61K 31/047* (2013.01); *A61K 31/05* (2013.01); *A61K 31/192* (2013.01); *A61K 31/25* (2013.01); *A61K 31/60* (2013.01); *A61K 31/7016* (2013.01); *A61K 31/717* (2013.01); *A61K 31/718* (2013.01); *A61K 39/395* (2013.01); *A61K 39/3955* (2013.01); *A61K 39/39516* (2013.01); *A61K 47/02* (2013.01); *A61K 47/12* (2013.01); *A61K 47/183* (2013.01); *A61K 47/36* (2013.01); *A61P 17/00* (2018.01); *C07K 16/06* (2013.01); *C07K 16/241* (2013.01)

(58) Field of Classification Search
None
See application file for complete search history.

(56) References Cited

U.S. PATENT DOCUMENTS

| | | |
|---|---|---|
| 8,052,645 B2 | 11/2011 | Slate et al. |
| 8,177,749 B2 | 5/2012 | Slate et al. |
| 8,920,374 B2 | 12/2014 | Bokelman et al. |
| 9,302,002 B2 | 4/2016 | Manning et al. |
| 9,393,305 B2 | 7/2016 | Manning et al. |
| 9,453,067 B2 | 9/2016 | Deutel et al. |
| 9,649,383 B2 | 5/2017 | Kashi et al. |
| 9,662,396 B2 | 5/2017 | Manning et al. |
| 9,700,595 B2 | 7/2017 | Lee et al. |
| 9,801,942 B2 | 10/2017 | Manning et al. |
| 2013/0108632 A1 | 5/2013 | Manning et al. |
| 2013/0108634 A1 | 5/2013 | Manning et al. |
| 2014/0199303 A1 | 7/2014 | Choi et al. |
| 2014/0255400 A1 | 9/2014 | Maloney et al. |
| 2015/0125532 A1 | 5/2015 | Manning et al. |
| 2015/0283241 A1 | 10/2015 | Apte-Deshpande et al. |
| 2016/0106844 A1 | 4/2016 | Bañado et al. |
| 2017/0348225 A1 | 12/2017 | Freitag et al. |
| 2018/0037642 A1 | 2/2018 | Arakawa et al. |

FOREIGN PATENT DOCUMENTS

| | | |
|---|---|---|
| WO | 2016033496 A1 | 3/2016 |
| WO | 2016033507 A2 | 3/2016 |

OTHER PUBLICATIONS

Portman et al. 'Etanercept as adjunctive treatment for acute kawasaki disease: Study design and rationale.' American Heart Journal vol. 161, Issue 3, Mar. 2011, pp. 494-499.*
Chouetier et al. A Prospective Open-Label Trial of Etanercept as Adjunctive Therapy for Kawasaki Disease . J Pediatr. Dec. 2010 ; 157(6): 960-966.e1. doi: 10.1016/j.jpeds.2010.06.014.*
https://www.accessdata.fda.gov/drugsatfda_docs/label/2008/enbrel_pi.pdf.*
https://www.accessdata.fda.gov/drugsatfda_docs/label/2016/761042lbl.pdf.*
"Enbrel label", Nov. 2017.
"Erelzi label", Aug. 2016.
Holman, R. C., et al., "Kawasaki Syndrome Hospitalizations Among Children in Hawaii and Connecticut", Arch Pediatr Adolesc Med. 154(8), Aug. 2000, 804-808.
McCrindle, B. W., et al., "Coronory Artery Involvement in Children With Kawasaki Disease—Risk Factors From Analysis of Serial Normalized Measurements", Circulation 116(2), 2007, 174-179.
McCrindle, B. W., et al., "Diagnosis, Treatment, and Long-Term Management of Kawasaki Disease—A Scientific Statement for Health Professionals From the American Heart Association", Circulation 135(17), 2017, e927-e999.

(Continued)

*Primary Examiner* — Nora M Rooney
(74) *Attorney, Agent, or Firm* — Saul Ewing Arnstein & Lehr LLP; Domingos J. Silva; Dennis Ostrovsky

(57) ABSTRACT

The present invention relates to the discovery that etanercept reduces the rate of resistance to intravenous gamma globulin (IVIG) in subjects with acute Kawasaki disease (KD). In certain embodiments, the co-administration of etanercept and IVIG more effectively treats acute KD in subjects older than 12 months than IVIG alone. In other embodiments, the co-administration of etanercept and IVIG ameliorates coronary artery dilation in high risk subjects.

59 Claims, 12 Drawing Sheets

Specification includes a Sequence Listing.

(56) References Cited

OTHER PUBLICATIONS

Newburger, J. W., et al., "Diagnosis, Treatment, and Long-Term Management of Kawasaki Disease: A Statement of Health Professionals From the Committee on Rheumatic Fever, Endocarditis, and Kawasaki Disease, Council on Cardiovascular Disease in the Young, American Heart Association", Pediatrics 114(6), Dec. 6, 2004, 1708-1733.

Newburger, J. W., et al., "Randomized Trial of Pulsed Corticosteroid Therapy for Primary Treatment of Kawasaki Disease", N Engl J Med. 356(7), Feb. 15, 2007, 663-675.

Porcalla, A. R., et al., "The Epidemiology of Kawasaki Disease in an Urban Hospital: Does African American Race Protect Against Coronary Artery Aneurysms?", Pediatric Cardiology 26(6), 2005, 775-781.

Rosenfeld, A., et al., "Kawasaki disease in infants less than one year of age", J. Pediatrics 126(4), 1995, 524-529.

Mastrangelo, G., et al., "Kawasaki disease in infants less than one year of age: an Italian cohort from a single center", BMC Pediatrics 19:321, 2019, 1-7.

\* cited by examiner

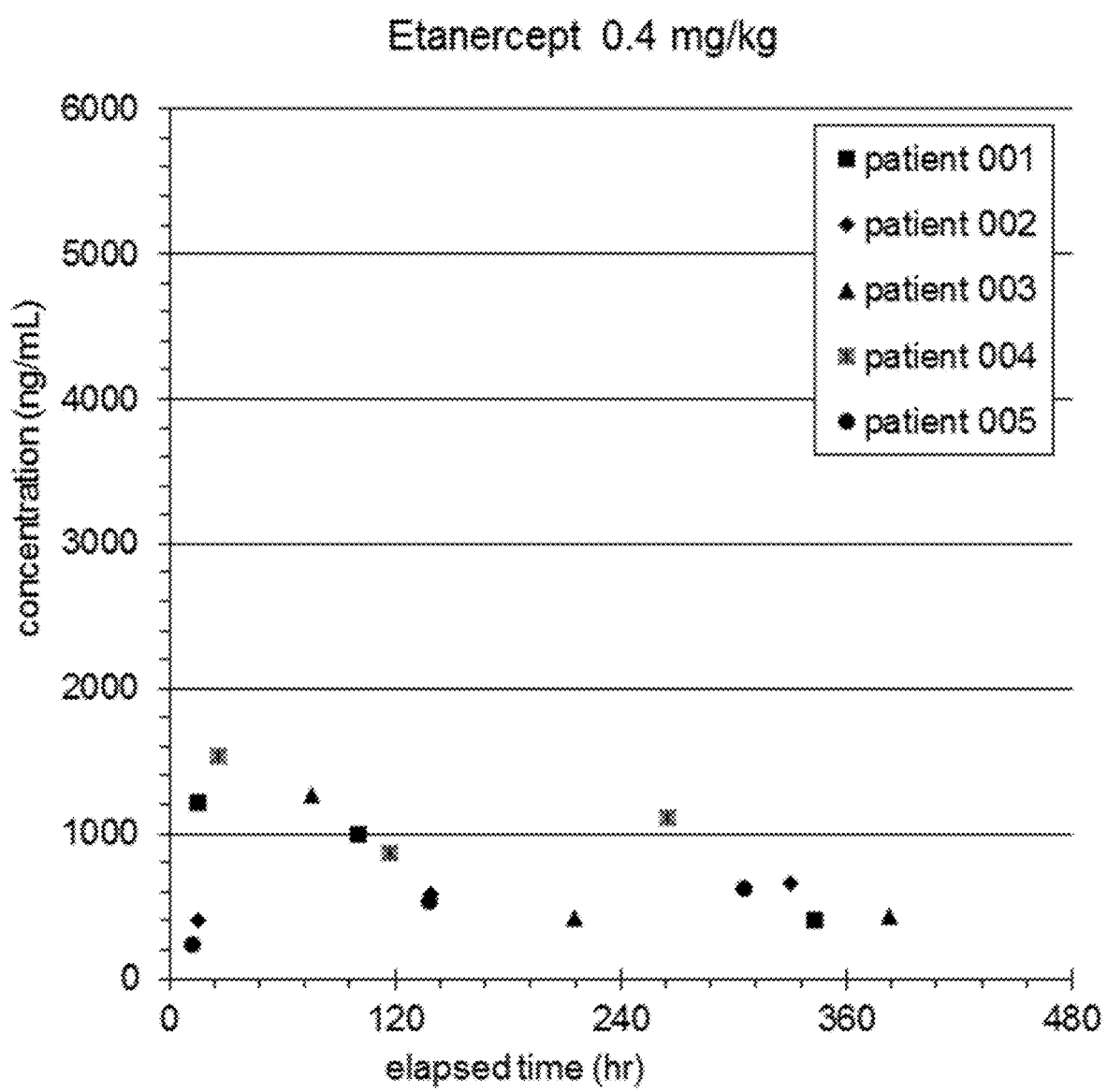

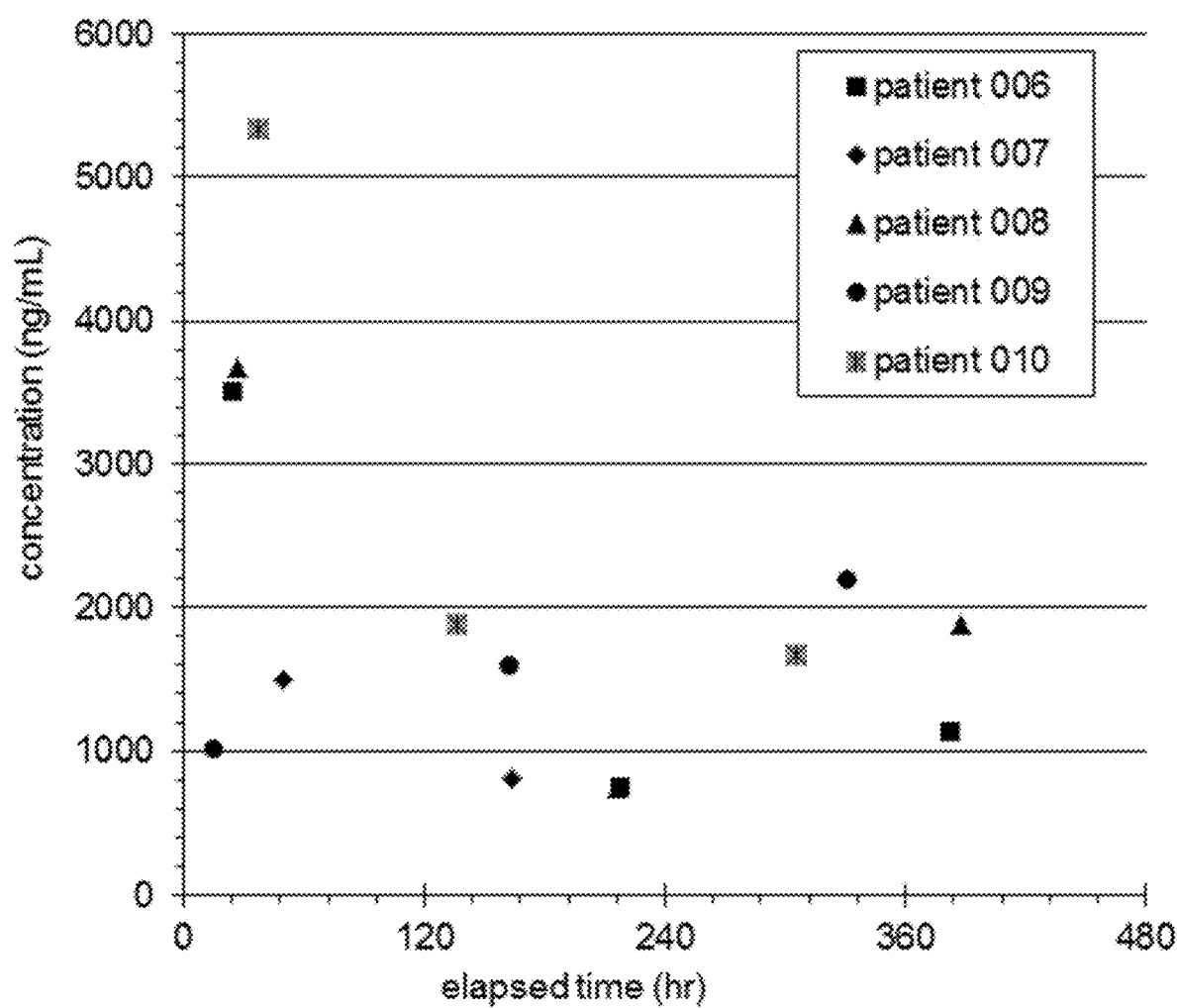

LMCA

LAD

RCA

LMCA

LAD

RCA

SEQUENCE LISTING

```
<160> NUMBER OF SEQ ID NOS: 1

<210> SEQ ID NO 1
<211> LENGTH: 467
<212> TYPE: PRT
<213> ORGANISM: Artificial Sequence
<220> FEATURE:
<223> OTHER INFORMATION: Chemically synthesized

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175
```

```
Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
        210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465
```

METHODS OF TREATING KAWASAKI DISEASE

CROSS-REFERENCE TO RELATED APPLICATION

This application claims the benefit under 35 U.S.C. § 119(e) of U.S. Provisional Patent Application Ser. No. 62/666,316 filed May 3, 2018, the disclosure of which is incorporated herein by reference in its entirety.

STATEMENT REGARDING FEDERALLY SPONSORED RESEARCH OR DEVELOPMENT

This invention was made with government support under grant number FD 003526-01 awarded by U.S. Food and Drug Administration (Department of Health and Human Services). The government has certain rights in the invention.

BACKGROUND OF THE INVENTION

Kawasaki Disease (KD, also known as mucocutaneous lymph node syndrome) is an acute inflammatory syndrome in children, and is characterized by fever and signs of vasculitis. Although self-limited in duration, KD can produce long-standing coronary artery pathology, including vessel dilation and aneurysms. Intraluminal thrombosis and/or stenosis can develop within afflicted coronaries, and lead to cardiovascular morbidity in young patients. Thus, KD is the leading cause of acquired heart disease in children in industrial nations.

Standard therapy is high dose intravenous gamma globulin (IVIG) and aspirin provided within the first 10 days after fever onset. This treatment is directed at eradicating the inflammation using fever as the principal clinical surrogate. However, fever either does not resolve or recurs in 10 to 25% of patients following the initial IVIG infusion. Individuals displaying fever resistance to IVIG (IVIG-resistant) demonstrate substantially higher odds (~10:1) than responsive patients for developing persistent coronary artery disease. The IVIG-resistant patients subsequently require secondary rescue therapy, again directed at eradicating fever and reducing inflammation. Clinical benefit from existing secondary treatments, such as repeat IVIG infusion, has not been validated by clinical trials.

There remains a need in the art for novel therapies for the treatment of KD. The present invention meets these needs.

BRIEF SUMMARY OF THE INVENTION

The invention provides a method of treating acute Kawasaki Disease (KD) in a human subject in need thereof. The invention further provides a method of reducing or preventing IVIG resistance in a subject being administered IVIG for the treatment of KD. The invention further provides a method of ameliorating or preventing progression, or promoting regression, of coronary artery dilation in a subject suffering from KD.

In certain embodiments, the method comprises administering to the subject a therapeutically effective amount of intravenous gamma globulin (IVIG) and a therapeutically effective amount of etanercept. In other embodiments, the method comprises administering to the subject a therapeutically effective amount of etanercept.

In certain embodiments, the subject is at least about 2 months old. In yet other embodiments, the subject is at least about 12 months old.

In certain embodiments, the subject is administered about 0.4 mg/kg to about 2 g/kg IVIG. In other embodiments, the subject is administered the IVIG over a period of about 10 hours. In yet other embodiments, the subject is administered the IVIG intravenously.

In certain embodiments, the subject is administered at least one dose of about 0.4 mg/kg to about 1.6 mg/kg etanercept. In other embodiments, the subject is administered at least one dose of about 0.4 mg/kg to about 0.8 mg/kg etanercept. In yet other embodiments, administration of the etanercept affords a blood serum steady state concentration of about 600 ng/ml to about 5,000 ng/ml etanercept in the subject. In yet other embodiments, the subject is administered the etanercept at least once a week. In yet other embodiments, the subject is administered the etanercept once a week. In yet other embodiments, the subject is administered the etanercept twice a week. In yet other embodiments, the subject is administered at least three doses of about 0.8 mg/kg etanercept each, wherein the at least three doses are administered about 4 to about 10 days apart from each other. In yet other embodiments, the subject is administered the etanercept parenterally. In yet other embodiments, the subject is administered the etanercept subcutaneously.

In certain embodiments, the etanercept is formulated as part of a pharmaceutical composition further comprising at least one pharmaceutically acceptable carrier. In other embodiments, the pharmaceutical composition does not comprise a buffer. In yet other embodiments, the pharmaceutical composition further comprises at least one buffer. In yet other embodiments, the pharmaceutical composition comprises water. In yet other embodiments, the pharmaceutical composition further comprises at least one additional compound selected from the group consisting of benzyl alcohol, mannitol, sorbitol, xylitol, sucrose, lactose, starch, cellulose, gelatin, polyethylene glycol, and tris(hydroxymethyl)aminomethane (tromethamine). In yet other embodiments, the pharmaceutical composition comprises etanercept, mannitol, sucrose, tris(hydroxymethyl)aminomethane, and a sterile bacteriostatic aqueous solution comprising benzyl alcohol. In yet other embodiments, the pharmaceutical composition comprises etanercept, mannitol, sucrose, tris(hydroxymethyl)aminomethane in a ratio (w:w:w:w) of about 25:40:10:1.25. In yet other embodiments, the pharmaceutical composition comprises etanercept, citric acid, sodium citrate, sodium chloride, sucrose, and lysine. In yet other embodiments, the pharmaceutical composition comprises etanercept, citric acid, sodium citrate, sodium chloride, sucrose, and lysine in a ratio (w:w:w:w) of about 33.3:0.52:9.0:1:6.7:3.1. In yet other embodiments, the pharmaceutical composition comprises sterile bacteriostatic water comprising about 0.9% benzyl alcohol. In yet other embodiments, the pharmaceutical composition comprises etanercept, NaCl, L-arginine, sucrose and water. In yet other embodiments, the pharmaceutical composition comprises about 50 mg/mL etanercept, about 120 mM NaCl, about 25 mM L-arginine, about 1% (w/v) sucrose, and water.

In certain embodiments, the subject is further administered aspirin, salicylic acid, or any salts, esters, or solvates thereof.

In certain embodiments, the method treats or prevents fever caused by KD in the subject.

In certain embodiments, the method does not cause or trigger any significant adverse event in the subject.

In certain embodiments, the method ameliorates progression of coronary artery dilation in high-risk subjects exhibiting dilation or aneurysm before treatment.

In certain embodiments, the method reduces IVIG resistance in the subject.

In certain embodiments, the IVIG is administered to the subject before the etanercept. In other embodiments, the IVIG is administered to the subject after the etanercept. In yet other embodiments, the etanercept is administered to the subject at any point during the course of acute KD. In yet other embodiments, the subject is African American or non-Hispanic White. In yet other embodiments, the subject is a high-risk subject exhibiting blood vessel dilation or aneurysm. In yet other embodiments, the subject has a coronary echocardiogram z-score >2.5.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIGS. 1A-1B are graphs showing data from patients in a preliminary study that received one 0.4 mg/kg etanercept dose per week (FIG. 1A), or one 0.8 mg/kg etanercept dose per week (FIG. 1B) starting immediately after IVIG infusion. Steady state therapeutically effective levels of etanercept were maintained in subjects given the 0.8 mg/kg doses after 1 week.

FIGS. 5A-5C report coronary artery measurements for the left main coronary artery (LMCA), left anterior descending artery (LAD) and right coronary artery (RCA), respectively, in mm for each patient group. FIGS. 5D-5F report z-scores for the left main coronary artery (LMCA), left anterior descending artery (LAD) and right coronary artery (RCA), respectively. Boxes enclose the $25^{th}$ to $75^{th}$ percentile, center lines represent the median and tails represent the $5^{th}$ and $95^{th}$ percentiles. Statistical outliers are not shown. Minima and maxima are as follows: for LMCA z-score, −1.18 and 17.20 for etanercept at baseline, −1.58 and 18.90 for etanercept at visit 5, −1.67 and 10.56 for placebo at baseline, −2.20 and 9.83 for placebo at visit 5; for LAD z-score, −2.09 and 16.45 for etanercept at baseline, −2.16 and 17.19 for etanercept at visit 5, −1.63 and 25.02 for placebo at baseline, −2.98 and 25.10 for placebo at visit 5; for RCA z-score, −1.52 and 9.47 for etanercept at baseline, −1.94 and 9.08 for etanercept at visit 5, −1.05 and 28.28 for placebo at baseline, −1.86 and 27.55 for placebo at visit 5.

DETAILED DESCRIPTION OF THE INVENTION

Figure 2:
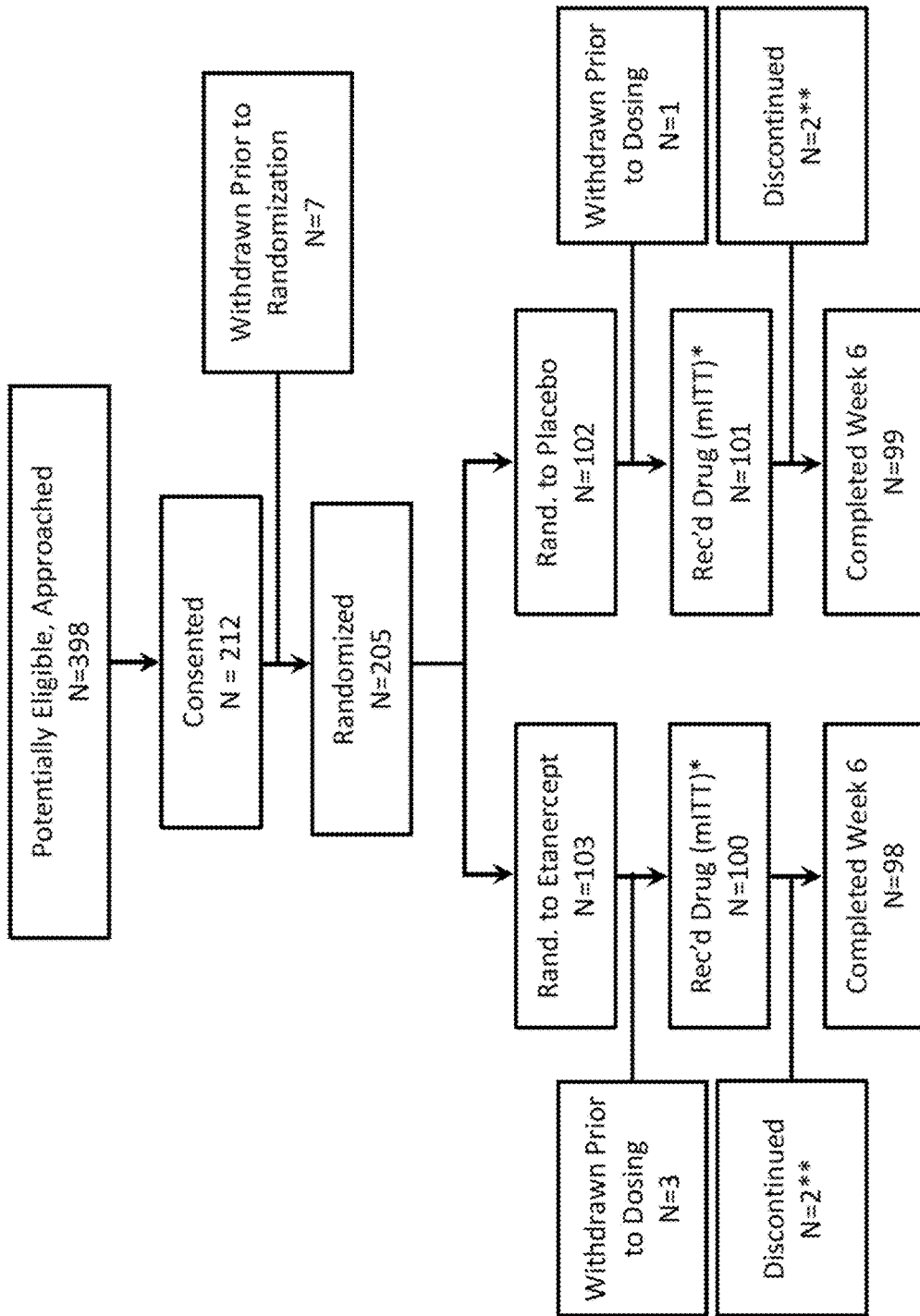
FIG. 2 is a flow chart outlining the approach, consent, randomization, and follow-up of participants in a Kawasaki Disease treatment study. A total of four randomized patients withdrew prior to dosing. Two hundred and one received study medication, four received at least initial dose but did not receive second or third dose. The four that did not receive additional doses were included in the modified intention to treat analyses.

The present invention relates to the discovery that etanercept reduces the rate of resistance to intravenous gamma globulin (IVIG) in subjects with acute Kawasaki Disease (KD). In certain embodiments, co-administration of etanercept and IVIG more effectively treats acute KD in subjects older than 12 months than administration of IVIG alone (in the absence of etanercept). In other embodiments, co-administration of etanercept and IVIG ameliorates coronary artery dilation in high risk subjects (subjects with baseline z-scores greater than 2.5). In yet other embodiments, co-administration of etanercept and IVIG is particularly effective in non-Hispanic white and African-American subjects suffering from KD.

Methods

In one aspect, the invention provides a method of treating acute KD in a subject in need thereof. In another aspect, the invention provides a method of reducing IVIG resistance in a subject suffering from KD and being treated with IVIG. In another aspect, the invention provides a method of ameliorating progression of coronary artery dilation in a subject suffering from KD. In certain embodiments, the subject is a high-risk subject exhibiting dilation or aneurysm.

In certain embodiments, the method comprises administering to the subject a therapeutically effective amount of etanercept. In other embodiments, the method comprises administering to the subject a therapeutically effective amount of intravenous gamma globulin (IVIG), wherein the subject is further administered a therapeutically effective amount of etanercept.

In certain embodiments, the subject is a human. In other embodiments, the subject is at least 2 months old, at least 3 months old, at least 4 months old, at least 5 months old, at least 6 months old, at least 7 months old, at least 8 months old, at least 9 months old, at least 10 months old, at least 11 months old, at least 12 months old, or any age thereinbetween. In yet other embodiments, the subject is not less than 12 months old. In yet other embodiments, the subject is younger than 3 years old, 6 years old, 9 years old, 12 years old, 15 years old, 18 years old, 21 years old, 24 years old, or any ages thereinbetween. In yet other embodiments, the subject is an infant, a toddler, a child, a juvenile, an adolescent, or a young adult.

In certain embodiments, the methods of the invention are effective in subjects of any heritage. In other embodiments, the methods of the invention are effective in subjects having at least partial African-American heritage. In yet other embodiments, the methods of the invention are effective in subjects having at least partial non-Hispanic white or Caucasian heritage.

In certain embodiments, the therapeutically effective amount of IVIG comprises about 0.4 mg/kg to about 2 g/kg IVIG. In other embodiments, the therapeutically effective amount of IVIG is administered to the subject over a period of time. In yet other embodiments, the therapeutically effective amount of IVIG is administered to the subject over about 10 hours.

In certain embodiments, the therapeutically effective amount of IVIG is administered once during the treatment period. In other embodiments, the therapeutically effective amount of IVIG is administered at least twice during the treatment period. In yet other embodiments, the therapeutically effective amount of IVIG is administered by day 10 of the onset of fever in KD patients. In yet other embodiments, the therapeutically effective amount of IVIG is administered twice during the treatment period, wherein the first dose is administered by day 10 of the onset of fever and the second dose is administered by day 12 of the onset of fever in KD patients. In yet other embodiments, the therapeutically effective amount of IVIG is administered to the subject intravenously.

In certain embodiments, the therapeutically effective amount of etanercept comprises at least one dose of about 0.4 mg/kg, or about 0.8 mg/kg. In other embodiments, the therapeutically effective amount of etanercept comprises up to about 1.6 mg/kg etanercept. In other embodiments, the therapeutically effective amount of etanercept comprises at least one dose of about 0.4 mg/kg to about 0.8 mg/kg etanercept, or about 0.4 mg/kg to about 1.6 mg/kg etanercept. In yet other embodiments, each dose of etanercept is not to exceed about 50 mg/dose etanercept.

In certain embodiments, the therapeutically effective amount of etanercept administered to the subject is sufficient to maintain a blood serum steady state concentration of about 600 ng/ml to about 5,000 ng/ml of etanercept. In other embodiments, the therapeutically effective amount of etanercept administered to the subject affords a blood serum steady state concentration of about 2,100 ng/ml of etanercept.

In certain embodiments, the therapeutically effective amount of etanercept is administered at least once per week to the subject. In other embodiments, the therapeutically effective amount of etanercept is administered at least twice per week to the subject.

In certain embodiments, the therapeutically effective amount of etanercept is administered at least once per week for three weeks, for about four weeks, for about five weeks, or for about six weeks.

In certain embodiments, the therapeutically effective amount of IVIG and the therapeutically effective amount of etanercept are administered concurrently. In other embodiments, the therapeutically effective amount of etanercept is added to the composition comprising the therapeutically effective amount of IVIG. In yet other embodiments, the therapeutically effective amount of IVIG and the therapeutically effective amount of etanercept are coformulated. In yet other embodiments, the therapeutically effective amount of IVIG and the therapeutically effective amount of etanercept are administered sequentially. In yet other embodiments, the therapeutically effective amount of IVIG is administered before the therapeutically effective amount of etanercept is administered. In yet other embodiments, the therapeutically effective amount of IVIG is administered after the therapeutically effective amount of etanercept is administered.

In certain embodiments, the therapeutically effective amount of IVIG and the therapeutically effective amount of etanercept are administered at any point during the course of acute KD. In other embodiments, the therapeutically effective amount of IVIG and the therapeutically effective amount of etanercept are administered after a diagnosis of KD is determined. In yet other embodiments, the therapeutically effective amount of IVIG and the therapeutically effective amount of etanercept are administered when fever continues during the course of acute KD. In yet other embodiments, the therapeutically effective amount of IVIG and the therapeutically effective amount of etanercept are administered at the first sign or symptom of KD. In yet other embodiments, the therapeutically effective amount of IVIG and the therapeutically effective amount of etanercept are administered at any later points during the course of acute KD, at least up to the disappearance of at least one sign or symptom of KD.

In certain embodiments, the therapeutically effective amount of etanercept comprises at least three doses of about 0.8 mg/kg etanercept each. In other embodiments, the at least three doses are administered about 4 to about 10 days apart. In yet other embodiments, the at least three doses are administered about 7 days apart. In yet other embodiments, the therapeutically effective amount of etanercept comprises at least six doses of about 0.8 mg/kg etanercept each, administered over at least six weeks.

In certain embodiments, the therapeutically effective amount of etanercept is administered subcutaneously. In other embodiments, the therapeutically effective amount of etanercept is administered intravenously.

In certain embodiments, the method further comprises administering to the subject a therapeutically effective amount of aspirin or a salt or solvate thereof. In certain embodiments, the therapeutically effective amount of aspirin can be determined by a medical professional or physician. In other, non-limiting embodiments, the therapeutically effective amount of aspirin comprises about 1 mg/kg/day to about 100 mg/kg/day. In yet other embodiments, the therapeutically effective amount of aspirin is about 80 mg/kg/day to about 100 mg/kg/day early in the onset of Kawasaki Disease. In yet other embodiments, the therapeutically effective amount of aspirin is about 3 mg/kg/day to about 5 mg/kg/day once symptoms of Kawasaki Disease begin to subside. In yet other embodiments, the therapeutically effective amount of aspirin is about 80 mg/kg/day to about 100 mg/kg/day for about the first 24 to 72 hours of treatment. In yet other embodiments, the therapeutically effective amount of aspirin is administered to the subject in at least one dose per day. In yet other embodiments, the therapeutically effective amount of aspirin is administered to the subject in at least two doses per day, at least three doses per day, or at least four doses per day.

In certain embodiments, the method further comprises administering to the subject a therapeutically effective amount of salicylic acid or a salt, solvate or prodrug (such as an ester thereof) thereof.

In certain embodiments, administration of etanercept prevents or lessens refractoriness of IVIG treatment in the subject as compared to treatments wherein etanercept is not administered. In certain embodiments, administration of etanercept reduces the number of patients with persistent or recrudescent fever at least 36 hours and <7 days after completion of first IVIG infusion. In certain embodiments, the subject is administered at least three doses of etanercept, each dose is from about 0.4 mg/kg to about 0.8 mg/kg, and the at least three doses are administered about 4 to about 10 days apart from each other. In certain embodiments, the subject is administered three doses of etanercept about 4 to about 10 days apart from each other, each at a dose of about 0.8 mg/kg. In other embodiments, administration of etanercept increases the effectiveness of the IVIG treatment in treating KD.

In certain embodiments, the method treats or prevents fever caused by KD in the subject. In other embodiments, the method treats or prevents fever caused by KD in the subject wherein the fever is at least as high as about 38° C. (100.4° F.).

In certain embodiments, the method does not cause or trigger any significant adverse events in the subject.

In certain embodiments, the method ameliorates progression of coronary artery dilation in high-risk subjects exhibiting dilation or aneurysm before treatment. In certain embodiments, the subjects have a coronary echocardiogram z-score >2.5. In certain embodiments, the subject is administered at least 6 doses of etanercept about 7 days apart from each other. In certain embodiments, the etanercept is administered at a dose of from about 0.4 mg/kg to about 1.6 mg/kg. In certain embodiments, the etanercept is administered for about 6 weeks at a weekly dose of from about 0.4 mg/kg to about 1.6 mg/kg.

Pharmaceutical Compositions Comprising Etanercept

In certain embodiments, the etanercept is formulated as part of a pharmaceutical composition, further comprising at least one pharmaceutically acceptable carrier. In other embodiments, the pharmaceutical composition further comprises at least one excipient. In yet other embodiments, the pharmaceutical composition further comprises at least one buffer (e.g., phosphate buffer and citric buffer). In yet other embodiments, the pharmaceutical composition comprises no buffer (buffer free). In yet other embodiments, the pharmaceutical composition comprises water. In yet other embodiments, the pharmaceutical composition further comprises at least one additional compound selected from the group consisting of benzyl alcohol, amino acid (e.g., arginine, glycine, lysine, proline and histidine), tonicity modifier (e.g., sodium chloride and magnesium chloride), polyol (e.g., mannitol, sorbitol, xylitol), sugar (e.g., sucrose, lactose), starch, cellulose, gelatin, polyethylene glycol, and tris(hydroxymethyl)aminomethane (tromethamine). In certain embodiments, the pharmaceutical composition comprises between 40 mg/mL and 100 mg/mL or between about 25 mg/mL to about 75 mg/mL etanercept. In certain embodiments, the pharmaceutical composition comprises about 50 mg/mL etanercept.

In certain embodiments, the pharmaceutical composition comprises etanercept, mannitol, sucrose, tris(hydroxymethyl)aminomethane, and a sterile bacteriostatic aqueous solution comprising benzyl alcohol. In other embodiments, the pharmaceutical composition comprises etanercept, mannitol, sucrose, tris(hydroxymethyl)aminomethane in a ratio (w:w:w:w) of about 25:40:10:1.25. In yet other embodiments, the pharmaceutical composition comprises sterile bacteriostatic water comprising about 0.9% benzyl alcohol.

In certain embodiments, the pharmaceutical composition comprises etanercept, arginine, sucrose, and sodium chloride. In certain embodiments, the pharmaceutical composition comprises between 75 mM and 150 mM NaCl, between 5 mM and 100 mM arginine, between 0.5% and 2% (w/v) sucrose, and between 40 mg/mL and 100 mg/mL etanercept, less than 2.0 mM of a standard buffering agent, and the pH of the composition is between 6.1 and 6.5. In certain embodiments, the pharmaceutical composition consisting essentially of about 50 mg/mL etanercept, about 120 mM NaCl, about 25 mM L-arginine, about 1% (w/v) sucrose, and water.

In certain embodiments, the pharmaceutical composition comprises etanercept, from 25 mM to 120 mM of a citrate buffer, and from 15 mM to 100 mM of lysine or proline or a pharmaceutically acceptable salt thereof. In certain embodiments, the pharmaceutical composition comprises about 50 mg/mL etanercept, citric acid, sodium citrate, sodium chloride, sucrose, lysine, and the pH of the composition is between 6.1 and 6.5. In other embodiments, the pharmaceutical composition comprises etanercept, citric acid, sodium citrate, sodium chloride, sucrose, and lysine in a ratio (w:w:w:w) of about 33.3:0.52:9.0:1:6.7:3.1.

In certain embodiments, the pharmaceutical composition comprises etanercept, 1 to about 10 wt. % of a sugar, up to about 10 wt. % of a polyol that differs from the sugar, about 1 mM to about 30 mM sodium phosphate and is free or essentially free of arginine. In certain embodiments, the pharmaceutical composition comprises etanercept, 5 to 10 mM magnesium, with a pH of about 6.0 to 6.6 and is free or essentially free of arginine. In certain embodiments, pharmaceutical composition comprises etanercept, 1 mM to 20 mM magnesium chloride and is free of arginine.

In certain embodiments, the pharmaceutical composition does not comprise a buffer.

In other embodiments, the etanercept is formulated as part of a pharmaceutical composition as described in one or more of the following U.S. Patents or U.S. Patent Application Publications, all of which are incorporated herein by reference: U.S. Pat. Nos. 9,700,595; 9,302,002; 9,393,305; 9,801,942; 9,662,396; 9,649,383; and 9,453,067; and U.S. Patent Application Publication Nos. 2017/0348225; 2013/0108632; 2013/1011583; 2013/0108634; 2015/0125532; 2018/0037642; 2014/0199303; 2015/0283241; 2014/0255400 and 2016/0106844.

In certain embodiments, the pharmaceutical compositions comprising etancercept can be presented in unit dosage form, e.g., in ampoules or in single- or multi-dose containers. The container can be, for example, a single-use container, i.e., a container that holds one dose etanercept formulation. It is understood that a single-use container might contain a single dose plus enough extra to ensure that a full single dose can be administered to a patient from the container, but not so much extra that the container could be used to administer a second dose. Examples of containers suitable for use in certain aspects of the present invention (whether they be single-use or multiple-use containers) include vials, syringes, and auto-injectors. Examples of suitable auto-injectors include those found in U.S. Pat. Nos. 8,177,749, 8,052,645, and 8,920,374, in U.S. patent application Ser. Nos. 12/993,163, 13/269,750, 13/454,531, 14/112,479, 14/777,255, and 14/777,259, and in PCT Publications WO 2014/0089393, WO 2016/033496, and WO 2016/033507, each of which is incorporated herein by reference in its entirety.

In certain embodiments, the pharmaceutical compositions may, if desired, be presented in a vial, pack or dispenser device which may contain one or more unit dosage forms containing etanercept. In one embodiment the dispenser device can comprise a syringe having a single dose of the liquid formulation ready for injection. In another embodiment, the pharmaceutical composition is aliquoted into a cassette component for use with a reusable autoinjector. In other embodiments, the autoinjector comprises a means of wireless communication capable of transmitting information to a programmable device, such as, but not limited to, a computer or a mobile device. In yet other embodiments, the means of wireless communication is a BLUETOOTH® device. Yet another aspect of the invention, the pharmaceutical compositions can be provided packaged in or with an on-body injector device. In still another embodiment, the pharmaceutical compositions can be aliquoted into a drug product form suitable for a needleless injection device.

Administration/Dosing

The regimen of administration may affect what constitutes an effective amount. The therapeutic formulations may be administered to the patient after the onset of a disease and/or disorder contemplated herein. Further, several divided dosages, as well as staggered dosages may be administered daily or sequentially or may be a bolus injection. Further, the dosages of the therapeutic formulations may be proportionally increased or decreased as indicated by the exigencies of the therapeutic or prophylactic situation.

Administration of the compositions of the present invention to a human may be carried out using known procedures, at dosages and for periods of time effective to treat a disease and/or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician, having ordinary skill in the art may readily determine and prescribe the effective amount of the pharmaceutical composition required. For example, the physician could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease and/or disorder contemplated herein.

It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of the disease and/or disorder contemplated herein.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease and/or disorder contemplated herein.

Routes of administration of any of the compositions of the invention include parenteral, transdermal, intrathecal, epidural, intrapleural, intraperitoneal, subcutaneous, intramuscular, intradermal, intra-arterial, and intravenous. In certain embodiments, the IVIG is administered intravenously, and the etanercept is administered subcutaneously. It should be understood that the formulations and compositions that would be useful in the present invention are not limited to the particular formulations and compositions that are described herein.

In one embodiment, the compositions of the invention are formulated using one or more pharmaceutically acceptable excipients or carriers. In another embodiment, the pharmaceutical compositions of the invention comprise a therapeutically effective amount of a compound of the invention and a pharmaceutically acceptable carrier.

In certain embodiments, the etanercept is formulated as part of a pharmaceutical composition. In other embodiments, the etanercept is formulated as part of a pharmaceutical composition as described in one or more of the following issued U.S. Patents or U.S. Patent Application Publications, all of which are incorporated herein by reference: U.S. Pat. Nos. 9,700,595; 9,302,002; 9,393,305; 9,801,942; 9,662,396; 9,649,383; and 9,453,067; and U.S.

Patent Application Publication Nos. 2017/0348225; 2013/0108632; 2013/1011583; 2013/0108634; 2015/0125532; 2018/0037642; 2014/0199303; 2015/0283241; 2014/0255400 and 2016/0106844.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Kits

In another aspect, the invention provides a kit for the treatment of Kawasaki Disease, the kit comprising a therapeutically effective amount of etanercept.

In certain embodiments, the therapeutically effective amount of etanercept is optionally formulated as part of a pharmaceutical composition further comprising at least one pharmaceutically acceptable carrier. Exemplary pharmaceutical compositions comprising etanercept are described elsewhere herein.

In certain embodiments, the kit comprises at least two doses of etanercept.

In certain embodiments, the kit further comprises at least one additional therapeutic agent for the treatment of Kawasaki Disease. In other embodiments, the at least one additional therapeutic agent is at least one selected from the group consisting of aspirin, salicylic acid or salts, solvates or prodrugs thereof.

In certain embodiments, the kit further comprises instructional materials containing instructions for performing the methods of the invention. In other embodiments, the kit further comprises at least one applicator for administering the compounds and compositions of the kit to a subject. In yet other embodiments, the kit further comprises at least one hypodermic needle and/or syringe.

In certain embodiments, the kit comprises at least one dose of etanercept in a single-dose prefilled syringe. In other embodiments, the single-dose prefilled syringe contains 0.5 mL of a colorless solution containing 25 mg of etanercept. In yet other embodiments, the single-dose prefilled syringe contains 1 mL of a colorless solution containing 50 mg of etanercept.

In certain embodiments, the kit comprises at least one dose of etanercept in a single-dose prefilled autoinjector syringe. In other embodiments, the single-dose prefilled autoinjector syringe is a SURECLICK® autoinjector or an equivalent device. In yet other embodiments, the single-dose prefilled autoinjector syringe contains 1 mL of a colorless solution containing 50 mg of etanercept.

In certain embodiments, the kit comprises at least one dose of etanercept in lyophilized powder form. In other embodiments, the lyophilized etanercept powder is contained within a vial. In yet other embodiments, the vial is a single or multi-dose vial comprising at least one dose of lyophilized etanercept powder. In yet other embodiments, the lyophilized etanercept powder can be reconstituted aseptically with sterile bacteriostatic water. In yet other embodiments, the kit comprises a vial adapter adapted and configured to aid addition of the sterile bacteriostatic water to lyophilized etanercept powder within the vial.

In certain embodiments, the kit comprises at least one dose of etanercept in a single-use vial as a sterile, preservative-free solution. In other embodiments, the single-use vial contains 0.5 mL sterile, preservative-free solution containing 25 mg etanercept.

In certain embodiments, the kit comprises at least one dose of etanercept in a prefilled cartridge for use with a reusable autoinjector device. In other embodiments, the autoinjector device is an AUTOTOUCH® reusable autoinjector or an equivalent device. In yet other embodiments, the prefilled cartridge contains 1 mL of a colorless solution containing 50 mg of etanercept.

In certain embodiments, the kit comprises an applicator comprising a means of wireless communication. In other embodiments, the applicator comprises a means of wireless communication capable of transmitting information to a programmable device, such as, but not limited to, a computer or a mobile device. In yet other embodiments, the applicator transmits an automated signal, whereby the automated signal signifies administration of etanercept from the applicator. In yet other embodiments, the means of wireless communication is a radio signal transmitter. In yet other embodiments, the means of wireless communication is a BLUETOOTH® device. In yet other embodiments, the applicator is a SURECLICK® autoinjector comprising a BLUETOOTH® device.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in pharmacology and pharmaceutical science are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "adverse event" or "AE" refers to is a symptom, sign, illness, or experience that develops or worsens in severity due to Kawasaki Disease and/or IVIG treatment.

In certain embodiments, the adverse event refers to at least one selected from the group consisting of abdominal pain, anemia, arthralgia, cough, diarrhea, emesis, epistaxis, headache, hematoma, pyrexia, rash, urticaria, and infection.

The term "applicator," as used herein, is meant to be any device including, but not limited to, a hypodermic syringe, a pipette, and the like, for administering the compounds and compositions of the invention to a subject.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, subcutaneous, oral, aerosol, parenteral, ophthalmic, nasal, pulmonary, and topical administration.

A "disease" as used herein is a state of health of a subject wherein the subject cannot maintain homeostasis, and wherein if the disease is not ameliorated then the subject's health continues to deteriorate.

A "disorder" as used herein in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, "etanercept" is a protein produced by recombinant DNA technology in a Chinese hamster ovary (CHO) mammalian cell expression system. It consists of 934 amino acids and has an apparent molecular weight of approximately 150 kilodaltons (Physicians Desk Reference, 2002, Medical Economics Company Inc.). A commercially available etanercept is known as ENBREL® (Immunex Inc., Thousand Oaks, Calif.). The full sequence of etanercept, expressed in CHO cells, is shown below in SEQ ID NO: 1. However, it is to be understood that modifications of this sequence, including additions and deletions (each up to 10%), are possible and can be used within the scope of the invention.

```
SEQ ID NO: 1:
  1    Leu-Pro-Ala-Gln-Val-Ala-Phe-Thr-Pro-Tyr-
 11    Ala-Pro-Glu-Pro-Gly-Ser-Thr-Cys-Arg-Leu-
 21    Arg-Glu-Tyr-Tyr-Asp-Gln-Thr-Ala-Gln-Met-
 31    Cys-Cys-Ser-Lys-Cys-Ser-Pro-Gly-Gln-His-
 41    Ala-Lys-Val-Phe-Cys-Thr-Lys-Thr-Ser-Asp-
                    -continued
 51    Thr-Val-Cys-Asp-Ser-Cys-Glu-Asp-Ser-Thr-
 61    Tyr-Thr-Gln-Leu-Trp-Asn-Trp-Val-Pro-Glu-
 71    Cys-Leu-Ser-Cys-Gly-Ser-Arg-Cys-Ser-Ser-
 81    Asp-Gln-Val-Glu-Thr-Gln-Ala-Cys-Thr-Arg-
 91    Glu-Gln-Asn-Arg-Ile-Cys-Thr-Cys-Arg-Pro-
101    Gly-Trp-Tyr-Cys-Ala-Leu-Ser-Lys-Gln-Glu-
111    Gly-Cys-Arg-Leu-Cys-Ala-Pro-Leu-Arg-Lys-
121    Cys-Arg-Pro-Gly-Phe-Gly-Val-Ala-Arg-Pro-
131    Gly-Thr-Glu-Thr-Ser-Asp-Val-Val-Cys-Lys-
141    Pro-Cys-Ala-Pro-Gly-Thr-Phe-Ser-Asn-Thr-
151    Thr-Ser-Ser-Thr-Asp-Ile-Cys-Arg-Pro-His-
161    Gln-Ile-Cys-Asn-Val-Val-Ala-Ile-Pro-Gly-
171    Asn-Ala-Ser-Met-Asp-Ala-Val-Cys-Thr-Ser-
181    Thr-Ser-Pro-Thr-Arg-Ser-Met-Ala-Pro-Gly-
191    Ala-Val-His-Leu-Pro-Gln-Pro-Val-Ser-Thr-
201    Arg-Ser-Gln-His-Thr-Gln-Pro-Thr-Pro-Glu-
211    Pro-Ser-Thr-Ala-Pro-Ser-Thr-Ser-Phe-Leu-
221    Leu-Pro-Met-Gly-Pro-Ser-Pro-Pro-Ala-Glu-
231    Gly-Ser-Thr-Gly-Asp-Glu-Pro-Lys-Ser-Cys-
241    Asp-Lys-Thr-His-Thr-Cys-Pro-Pro-Cys-Pro-
251    Ala-Pro-Glu-Leu-Leu-Gly-Gly-Pro-Ser-Val-
261    Phe-Leu-Phe-Pro-Pro-Lys-Pro-Lys-Asp-Thr-
271    Leu-Met-Ile-Ser-Arg-Thr-Pro-Glu-Val-Thr-
281    Cys-Val-Val-Val-Asp-Val-Ser-His-Glu-Asp-
291    Pro-Glu-Val-Lys-Phe-Asn-Trp-Tyr-Val-Asp-
301    Gly-Val-Glu-Val-His-Asn-Ala-Lys-Thr-Lys-
311    Pro-Arg-Glu-Glu-Gln-Tyr-Asn-Ser-Thr-Tyr-
321    Arg-Val-Val-Ser-Val-Leu-Thr-Val-Leu-His-
331    Gln-Asp-Trp-Leu-Asn-Gly-Lys-Glu-Tyr-Lys-
341    Cys-Lys-Val-Ser-Asn-Lys-Ala-Leu-Pro-Ala-
351    Pro-Ile-Glu-Lys-Thr-Ile-Ser-Lys-Ala-Lys-
361    Gly-Gln-Pro-Arg-Glu-Pro-Gln-Val-Tyr-Thr-
371    Leu-Pro-Pro-Ser-Arg-Glu-Glu-Met-Thr-Lys-
381    Asn-Gln-Val-Ser-Leu-Thr-Cys-Leu-Val-Lys-
391    Gly-Phe-Tyr-Pro-Ser-Asp-Ile-Ala-Val-Glu-
401    Trp-Glu-Ser-Asn-Gly-Gln-Pro-Glu-Asn-Asn-
411    Tyr-Lys-Thr-Thr-Pro-Pro-Val-Leu-Asp-Ser-
421    Asp-Gly-Ser-Phe-Phe-Leu-Tyr-Ser-Lys-Leu-
431    Thr-Val-Asp-Lys-Ser-Arg-Trp-Gln-Gln-Gly-
441    Asn-Val-Phe-Ser-Cys-Ser-Val-Met-His-Glu-
```

```
451    Ala-Leu-His-Asn-His-Tyr-Thr-Gln-Lys-Ser-

461    Leu-Ser-Leu-Ser-Pro-Gly-Lys
```

As used herein, the term "high-risk subject" regarding cardiological health, refers to individuals that exhibit blood vessel dilation and/or at least one aneurysm. In certain embodiments, the subjects have a coronary echocardiogram z-score >2.5.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

A patient experiencing "IVIG resistance" or variants thereof, is meant to refer to a subject suffering from Kawasaki Disease related fever that has not resolved within 36 hours of IVIG infusion. In certain embodiments, IVIG resistance is determined when a subject's body temperature remains above 38° C. 36 hours after IVIG administration. In certain embodiments, a treatment method that "reduces IVIG resistance" is a method that reduces the incidence rate of IVIG resistance.

The terms "patient," "subject" or "individual" are used interchangeably herein, and refer to any human, amenable to the methods described herein. Preferably, the patient, individual or subject is a human pediatric patient. In certain embodiments, the subject is between about 0 years of age and about 16 years of age. In other embodiments, the subject suffers from KD.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

The following abbreviations are used herein: AA: African-American; AE: adverse event; AHA: American Heart Association; AAP: American Academy of Pediatrics; ASA: Aspirin; AST: aspartate aminotransferase; ALT: alanine aminotransferase; CBC: complete blood count; CHRMC: Children's Hospital and Regional Medical Center; CRP: C-reactive protein; DMC: Data Monitoring Committee; DNA: deoxyribonucleic acid; Echo: echocardiogram; EKG: electrocardiogram; ESR: erythrocyte sedimentation rate; FDA: Federal Drug Administration; Ig: immunoglobulin; IV: intravenous; IVIG: intravenous immunoglobulin; IRB: Institutional Review Board; KD: Kawasaki Disease; LAD: left anterior descending artery; LMCA: left main coronary artery; PK: pharmacokinetics; RCA: right coronary artery; SAE: serious adverse event; TNF: tumor necrosis factor; TNFR: tumor necrosis factor receptor.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and/or treatment conditions with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods
Participant Inclusion Criteria

The American Academy of Pediatrics and the American Heart Association (AHA/AAP) have published guidelines for epidemiological case definition. KD treatment, including IVIG and aspirin, is recommended for patients fitting these criteria. Generally, supportive laboratory data also exist including elevation of erythrocyte sedimentation rate and C reactive protein (CRP>3.0, although usually much higher). Thrombocytosis (platelet count >500,000) usually occurs in the second week.

Patients (age 2 months to 20 years) had to fit the standard epidemiological definition of acute KD as recommended by the joint AHA/AAP guidelines or fit criteria for diagnosis of incomplete KD as described below. Patients were enrolled only after a clinical decision to treat with IVIG had been made by the treating physician.

Patients were enrolled if they began IVIG infusion within 10-13 days of onset of illness with day 1 defined as the first day of fever. Patients were enrolled with greater than 10 days of fever upon written approval or email confirmation from the study Principal Investigator on a case by case basis.

Parents of subject or non-minor subject had to be able and willing to give written informed consent and comply with the requirements of the study protocol and had to authorize release and use of protected health information.

Patients fit American Heart Association, American Academy of Pediatrics guidelines for diagnosis of Kawasaki Disease if they exhibited a fever persisting at least 5 days and the presence of at least 4 principal features selected from:

1) Changes in extremities (Acute: Erythema of palms, soles; edema of hands, feet; Subacute: Periungual peeling of fingers);
2) Polymorphous exanthema;
3) Bilateral bulbar conjunctival injection without exudate;
4) Changes in lips and oral cavity: Erythema, lips cracking, strawberry tongue, diffuse injection of oral and pharyngeal mucosae; and
5) Cervical lymphadenopathy (1.5-cm diameter), usually unilateral;

In the presence of all 5 principal criteria, Kawasaki Disease diagnosis was made on day 4 of illness.

Patients with fever at least 5 days and 3 principal criteria were diagnosed with Kawasaki Disease when coronary artery abnormalities were detected by 2 dimensional echocardiography. A qualifying echocardiogram is defined as coronary artery z score ≥2.5 in the proximal coronary artery or left anterior descending, or aneurysm by Japanese Ministry of Health criteria.

Patients with fever at least 5 days and 2-3 principal criteria without coronary artery abnormalities were diagnosed with Kawasaki Disease when the patient had a CRP of 3.0 mg or greater and 3 or more of the supplementary lab criteria listed below:
albumin <3.0 g/dL
anemia for age
elevation of alanine aminotransferase
platelets after 7 days >450,000/mm$^3$
white blood cell count >15,000/mm$^3$
urine >10 white blood cells/high-power field Drug Preparation and Administration Etanercept is a recombinant TNF receptor Fc Fusion protein. It is pharmacologically classified as a TNF antagonist, with the sole active ingredient being etanercept. Etanercept powder was reconstituted with sterile diluent supplied by Amgen, Inc. prior to its subcutaneous injection such that the final dosage achieved was 0.8 mg/kg. Each vial of powdered etanercept contained 25 mg etanercept, 40 mg mannitol, 10 mg sucrose, and 1.2 mg tromethamine. Etanercept is reconstituted aseptically with the Amgen-supplied Sterile Bacteriostatic water for Injection, USP (0.9% benzyl alcohol) so that the desired study dosage is met. Subjects are given subcutaneous injections of 0.8 mg/kg etanercept 3 times at weekly intervals, starting at initial diagnosis.

Administration and Treatment Procedures
Treatment Schedule

Etanercept 0.8 mg/kg (maximum 50 mg) or placebo was given within 48 hours of initiating IVIG infusion. Randomization was performed by internal Pharmacy, unblinded (see Pharmacy procedures). Placebo format is: Etanercept placebo (Amgen), TMS Lyo, B20 UnLBL 2 mL vial Pink Cap. Study schema and procedures are outlined below.

TABLE 1

Treatment Protocols

| TIME | 0 | 12-84 hours | 7 ± 3 days | 14 ± 3 days | 44 ± 4 days |
|---|---|---|---|---|---|
| Physical Exam | x | | x | x | x |
| Etanercept/Placebo | x | | x | x | |
| PK | x | x | x | x | |
| Cytokines | x | x | x | | |
| CBC | x | | x | x | x |
| CRP | x | | x | x | x |
| ESR | x | | | | |
| Echo | x | | | x | x |
| EKG | x | | | x | x |

TABLE 1-continued

Treatment Protocols

| TIME | 0 | 12-84 hours | 7 ± 3 days | 14 ± 3 days | 44 ± 4 days |
|---|---|---|---|---|---|
| AST, ALT | x | | x | x | |
| Albumin | x | | x | x | x |

Time 0 or baseline was defined as time first dose of study drug was given. Time 0 or baseline labs were almost always done before the patient consented to the study. These labs were optional unless the patient was qualifying into the study through supplementary lab data. In general, admission laboratory values used to confirm diagnosis of KD were used for the study, provided that they were within 24 hours prior to initiating IVIG. If a time zero lab value was not drawn as part of the clinical course prior to the patient enrolling in the study, it was not collected and was recorded as missing data. After enrollment, coordinators attempted to retrieve extra serum obtained along with admission laboratory studies. This serum was used for baseline pharmacokinetic assay, PK.

An EKG was normally done at time zero as part of clinical care. This EKG was optional; if an EKG was not performed at baseline it was not recorded as a protocol deviation.

Parents recorded temperature after discharge daily between 4 PM and 6 PM for two weeks, as well as if and when they believed the child had a fever, and notified the study coordinator if >38.0° C. If patient temperature >38° C. and the investigator or treating cardiologist felt the patient needed to be readmitted, an extra study visit occurred within 12-24 hours of re-admission with PE, CBC, CRP, ESR, Echo, and ECG. This extra visit concurred with clinical guidelines for standard of care. CBC included WBC with differential and platelet count. Parents were also to notify coordinator of any sign of infection. PK assay in the "24-84 hour" measurement was measured at time point 48 hours (window 12-48 hours) after Etanercept administration.

Failure to respond to IVIG was determined using the AHA guidelines: as persistent fever >38.0° C. extending beyond 36 hours after completion of IVIG infusion or recurrent fever >38.0° C. after 36 hours of completion of the initial IVIG infusion.

Visit 1 (Time 0)—Hospital

The patients were admitted into the hospital. Patients' families were referred to the research staff for study discussion and consent. The patients were screened for eligibility, study discussion was conducted, and consent was obtained. Assent was also obtained if deemed required by IRB.

All patients received standard treatment for KD as stated in the AHA-AAP guidelines. This included IVIG 2 g/kg over 10 hours or longer if interruptions occurred in the infusion and high dose ASA, administered at 80 to 100 mg/kg per day in 4 doses until patients had been afebrile for 48 hours. Subsequently, patients continued low dose aspirin (ASA) 3-5 mg/kg per day until 6 weeks or longer at the discretion of the treating Pediatric Cardiologist.

The blood for the baseline measurements was drawn with the IV start or from the IV line. Labs obtained upon hospital admission were used for baseline data. The PK blood sample was processed and stored for later shipping by the lab or study personnel, while the other blood samples were sent to the central hospital laboratory for processing and results. An Echo and EKG were performed. A nurse administered a subcutaneous injection of study drug or equivalent volume of placebo at the appropriate dosage 0.8 mg/kg (maximum 50 mg). Etanercept was administered within 48 hours after initiating IVIG therapy, and as early as possible. Etanercept was not given prior to starting IVIG infusion. After discharge, the parents of the patients were to record daily temperatures between 4 PM and 6 PM for the next two weeks in a log provided by the nurse coordinator. A thermometer was given to the family if not already available or provided by hospital and coordinator instructed patients regarding the proper procedure for taking and recording temperature. If the parents believed that their child had a fever, they were to record the child's temperature regardless of the time of day and notify the study coordinator if temperature was >38.0° C. If the study coordinator was unavailable the family was instructed to call the on-call cardiologist. If the child was readmitted, an extra study visit occurred within 12-24 hours of the patient being readmitted, and a physical exam, CBC, CRP, ESR, ECG, and Echo were completed. Parents were to notify the study coordinator if they found any signs of infection in the patient.

Visit 2 (12-84 Hours)—Hospital

This visit was optional, and would be timed within 12-84 hours of etanercept administration. If the intravenous line was still in place, or a blood draw was clinically indicated within this window, approximately 4 cc of blood was drawn for the PK test. A numbing agent was optionally used to decrease the discomfort associated with phlebotomy. The blood was sent to the laboratory for the necessary blood work. Patients were generally observed for 24 to 48 hours after completion of IVIG dose prior to discharge. Study investigators observed patients through their period in the hospital. Observation continued if patient hospitalization extended beyond that period for complications of disease or therapy until the patient was discharged.

Visit 3 (Day 7±72 Hours)—Clinic

A physical assessment and a blood draw (approximately 7 cc) were required about 7 days after initiating IVIG therapy. A nurse performed an abbreviated physical exam on each patient as part of the nursing assessment. A numbing agent was optionally used to decrease the discomfort associated with phlebotomy and/or study drug administration. The blood sample was sent to the laboratory for the tests listed in the study schema (Table 1), while study personnel processed the PK sample and stored it for later shipping. A nurse administered a subcutaneous injection of study medication at the appropriate dosage.

Visit 4 (Day 14±72 Hours)—Clinic

A physical exam and a blood draw (approximately 7 cc) were required about 14 days after initiating IVIG therapy. A numbing agent was optionally used to decrease the discomfort associated with phlebotomy and/or study drug administration. The blood sample was sent to the laboratory for the tests listed in the study schema (Table 1), while study personnel processed the PK sample and stored it for later shipping. An Echo and EKG were performed. A nurse administered a subcutaneous injection of study drug at the appropriate dosage.

Visit 5 (Day 44±4 Days)—Clinic

A physical exam and a blood draw (approximately 7 cc) were required 44 days after initiating IVIG therapy. The blood sample was sent to the laboratory for the tests listed in schema (Table 1). An Echo/EKG was performed. No study drug was administered.

Treatment for Refractoriness to IVIG

All patients who fit the requirements for refractoriness to IVIG (see Study Endpoints) received standard clinical treatment as determined by the attending physician. Standard treatment was usually a second dose of IVIG, as defined in the American Heart Association guidelines. Retreatment with IVIG did not interrupt the study and study medication should still be administered.

Follow-Up Echocardiogram Surveillance

Follow up data was collected for patients who had a positive echo (z score ≥2.5 or aneurysm) at visit 5 for 14 months following their diagnosis or until their echo normalized. De-identified visit notes and echocardiogram and angiogram reports that fell within this window were sent to the study sponsor.

Echocardiography

In order to maintain consistency with other U.S. clinical trials in KD, coronary artery dimensions were normalized for body surface area as z scores (SDs from a predicted normal mean). Coronary artery Z-scores were based on nonlinear regression equations derived from a normal non-febrile population, comprised of 221 healthy children aged 0 to 18 years seen in the noninvasive laboratory at Boston Children's Hospital for echocardiographic evaluation during the years 1987 to 2000. These patients had no evidence of structural or functional heart disease. Z-scores were determined for the left main coronary artery (LMCA), proximal left anterior descending (pLAD), and proximal right coronary artery (pRCA) using the following algorithms:

$$LMCA = 0.31747 \cdot (BSA^{0.36008}) - 0.02887, SD = 0.03040 + (0.01514 \cdot BSA)$$

$$pLAD = 0.26108 \cdot (BSA^{0.37893}) - 0.02852, SD = 0.01465 + (0.01996 \cdot BSA)$$

$$pRCA = 0.26117 \cdot (BSA^{0.39992}) - 0.02756, SD = 0.02407 + (0.01597 \cdot BSA)$$

where LMCA indicates left main coronary artery, in centimeters; pLAD, proximal anterior descending coronary artery, in centimeters; pRCA, proximal right coronary artery, in centimeters; and BSA, body surface area, in meters squared calculated by the Haycock method.

In order to limit interobserver variability, a central Echocardiography reader adjudicated these interpretations. Presence of coronary artery aneurysms was determined using Japanese Ministry of Health Criteria: aneurysm diameter 1.5 times the diameter of the vessel immediately proximal. All centers forwarded digital echocardiograms to the Seattle Center for central reading by a single observer. The single observer was a Pediatric Cardiologist trained at Boston Children's Hospital who spent an extra year in an imaging fellowship, prior to taking a faculty position at Children's Hospital and Regional Medical Center-University of Washington (CHRMC-UW). The single observer was intimately familiar with procedures used to develop z-scores from the cohort of patients at Boston Children's Hospital and provided consistency for the echo determinations.

IVIG Retreatment

The primary aim of this study was to determine if Etanercept (ENBREL®) 0.8 mg/kg given subcutaneously to patients with acute Kawasaki Disease reduced the incidence of IVIG refractoriness as defined in the joint American Heart Association and American Academy of Pediatrics Endorsed Clinical Report: "Refractory Kawasaki Disease will be defined as the persistence or recrudescence of fever (≥38.0° C. or 100.4° F.) at least 36 hours after the end of the IVIG infusion". Persistent or recrudescent fever was the sole criteria for determining the need for retreatment. The clinical decision was supported by persistent symptoms and persistent elevation or rebound of inflammatory parameters such as CRP. The protocol required waiting at least 36 hours after completing the first IVIG dose before initiating the second dose.

Standard Treatment

IVIG (2 g/kg) and aspirin (80-100 mg/kg Q6 hr until afebrile then 3-5 mg/kg/day) were standard treatment regiments for acute Kawasaki Disease. Their concomitant therapy was to be expected and permitted.

All patients with disease-related complications received standard care by their primary Pediatric Cardiologist and other treating physicians. This included anticoagulation therapy when the primary Cardiologist determined it was necessary. AHA/AAP guidelines recognize the use of various types of anti-coagulation. Low dose ASA as described above represents the primary antiplatelet therapy. Clopidogrel in combination with aspirin is more effective than either agent alone in preventing vascular events in both coronary and cerebral territories in adults (the Clopidogrel in Unstable Angina to Prevent Recurrent Events study). However, there is no evidence in children that this is effective therapy. Many Pediatric Cardiologists use heparin infusion often followed by Warfarin for rapidly expanding or giant coronary artery aneurysms.

The current protocol does not preclude their use. An adjunctive therapy for KD is hereby proposed; it does not require interference with standard of care and does not preclude concomitant medications. All medications prescribed by primary care providers are permitted.

Additionally, no live vaccine may be given for at least 11 months after receiving IVIG as recommended by the American Academy of Pediatrics.

Treatment with high dose steroids and/or infliximab during the course of the study was permitted if recommended by Rheumatology for the treatment of recurrent Kawasaki Disease.

The following medical therapies were not permitted for study participation:

Treatment with any TNFα antagonist or steroid within 48 hours prior to initiation of IVIG.

Current use of an investigational device or drug trial(s), or receipt of other investigational agent(s) within 28 days of baseline visit.

Prior or concurrent cyclophosphamide therapy.

Concurrent sulfasalazine therapy.

Concurrent isonicotinic acid hydrazide therapy.

Any live vaccine 30 days prior to, or during the study. Patient may be enrolled in the study 14 days after administration of Influenza mist vaccine.

Prior (within 3 months preceding enrollment) or concurrent use of immunosuppressive agents.

In addition, any medical therapies that may have caused harm to the patient, as judged by the patient's physician on a case-by-case basis, was not permitted.

Example 1: Preliminary Studies

Open Label Study.

An open label nonrandomized study evaluating safety and pharmacokinetics of Etanercept in patients aged 6 months to 5 years was performed. 12 patients were enrolled in the preliminary study. The first 5 patients received 0.4 mg/kg etanercept subcutaneously, and patients thereafter received 0.8 mg/kg. Doses were given within 12 hours of completing IVIG infusion, at 7 days and at 14 days (see Table 1). Demographics of patients are shown in Table 2.

TABLE 2

Demographics For Etanercept Subjects

| Subject | Weight (kg) | Age (months) |
|---|---|---|
| 1 | 16.1 | 46 |
| 2 | 13.1 | 25 |
| 3 | 13.9 | 27 |
| 4 | 6.9 | 9 |
| 5 | 31.4 | 67 |
| 6 | 9.9 | 11 |
| 7 | 12.0 | 35 |
| 8 | 23.5 | 55 |
| 9 | 14.5 | 41 |
| 10 | 7.7 | 11 |
| 11 | 15.7 | 57 |
| 12 | 12.2 | 27 |
| MEAN | 14.7 | 34.25 |
| STDEV | 6.8 | 19.3 |

Safety.

No patient required readmission after initial discharge. Two patients had mild upper respiratory infections associated with similar symptoms in family members after discharge; one of these had a single fever spike 3 weeks after IVIG treatment, which resolved quickly without treatment other than acetaminophen. One additional patient had otitis media, which required antibiotics. One patient vomited several times after eating "Chinese Food". Only one serious adverse event occurred. One patient was treated with IVIG and subsequently Etanercept. Although, the patient had 4 criteria and persistent fever qualifying for the diagnosis of Kawasaki Disease as well as negative blood cultures, he developed hydrocephalus caused by meningococcal meningitis. The patient was treated with antibiotics and recovered. The DMC and IRB agreed that this SAE was unrelated to Etanercept, but emphasized the importance of eliminating other infectious diseases, when making the diagnosis of KD.

Efficacy.

A protocol deviation resulted in one patient receiving a second dose of IVIG for a fever spike 12 hours after completing IVIG. Clinical care guidelines recommended no second dose until 36 hours after completing IVIG, as many patients have a brief post-IVIG fever spike. Otherwise, no other patient demonstrated IVIG refractoriness. According to prior studies, it was expected that at least two and possibly three patients would have demonstrated IVIG refractoriness in this group. Among the 4 eligible patients refusing enrollment, one patient demonstrated recrudescent fever, was readmitted and treated with a second dose of IVIG. Ten study patients showed normalization of CRP by the 7 day visit indication suppression of acute phase proteins.

Coronary artery z-scores are shown for each patient in Table 3. No patient showed new coronary artery dilation or aneurysm after etanercept. Three patients showed coronary aneurysm or dilation prior to etanercept. One of these was an 11 month old infant (Subject 4) with two large right coronary artery aneurysms at presentation, which persisted throughout the study. However, the other two patients showed resolution of CAD. This results in a 10% rate of CAD.

TABLE 3

Maximal Coronary Artery Z-Scores

| Subject | Baseline | 2-week | 6-week |
|---|---|---|---|
| 1 | 2.6 | 2.5 | 2.7 |
| 2 | 1.7 | 1.2 | 1.2 |
| 3 | 0.5 | −0.12 | −0.12 |
| 4* | 7.1 | 7.4 | 7.4 |
| 5 | 1 | 0.91 | 1.08 |
| 6 | 0.5 | 0.5 | 0.5 |
| 7 | 2 | 1.6 | 1.3 |
| 8 | 0.6 | 0.6 | 0.6 |
| 9 | 0.5 | −0.15 | −0.5 |
| 10 | 2.8 | 0.9 | NA |
| 11 | 0.7 | 0.7 | NA |
| Mean | 1.49 | 1.1 | |
| STDV | 1.864381244 | 2.011634 | |

Dose Rationale.

Etanercept is slowly absorbed after subcutaneous (SC) injection, and the absolute bioavailability is approximately 58% in adults (Nestorov, et al., 2005, Semin Arthritis Rheum. 34(5 Suppll):12-18). Etanercept has a relatively small volume of distribution of 12±6 and is slowly absorbed to reach its peak serum concentration about 50 hours after injection and cleared from the body with a reported median half-life of 115 hours. The recommended dosing regimen for juvenile rheumatoid arthritis (JRA) patients (4-17 years) at the time of etanercept's initial FDA approval was 0.4 mg/kg (up to 25 mg) twice weekly by SC injection. FDA approval has also been given for a doubled dose at half frequency (0.8 mg/kg, up to 50 mg, once weekly).

PK profiles collected for the two different drug doses used in the preliminary study are shown in FIGS. 1A-1B. The pharmacokinetic profiles for the 5 preliminary study patients, receiving 0.4 mg/kg weekly (FIG. 1A), showed lower than therapeutic levels, defined by $5^{th}$ to $95^{th}$% tile range as determined for JRA treatment. Steady state concentrations after 0.8 mg/kg after 1 week (FIG. 1B) were found to be within the simulated and therapeutic range calculated for the JRA group.

These results suggest that 0.8 mg/kg weekly is adequate to maintain levels within the therapeutic range defined by earlier JRA trials. The younger age of the KD patients did not appear to substantially affect absorption and metabolism of etanercept. Three enrolled patients less than 2 years of age showed similar pharmacokinetic profile to all other patients and JRA patients. These patients also showed no adverse events from Etanercept.

Example 2

(a) Trial Design

The effects of etanercept were tested in a Phase 3 multicenter, placebo-controlled, double blind investigator initiated randomized trial. The study received drug, and placebo from Amgen.

Study Endpoints

The primary endpoint was proportion of participants with fever persistence or recurrence greater than 36 hours and up to 7 days following completion of the IVIG infusion. Comparisons for IVIG non-response risk between placebo and treatment groups within important demographic subgroups: age (<1 year versus >1 year), gender, race and ethnicity (Non-Hispanic White, NHW; African American, AA; Asian, EAS, Hispanic, HIS) were preplanned. Echocardiographic coronary artery parameters served as secondary endpoints and were based on changes in absolute values according to an algorithm found in FIG. 3. Coronary artery dimensions were also normalized for body surface area as z scores (SDs from a predicted normal mean) based on published Boston criteria (McCrindle, et al., 2007, Circulation 116(2):174-179), and used as secondary endpoints by comparing the baseline visit to Week 6. Stratified analyses with the algorithm according to AHA defined (McCrindle, et al., 2017, Circulation 135(17):e927-e99; Porcalla, et al., 2005, Pediatric Cardiology 26(6):775-781) baseline CA dilation as a z score ≥2.5 or any aneurysm were also preplanned.

Participants

Eight pediatric academic centers were initiated for EATAK and enrolled patients. Participants aged 2 months to 18 years were required to meet the acute KD criteria as defined by the 2004 American Heart Association (AHA) guidelines (Newburger, et al., 2004, Pediatrics 114(6):1708-1733). Patients were eligible if their initial IVIG treatment initiated by day 10 after onset of fever or up to day 12 if fever continued and C-reactive protein elevated >3.0.

Pharmacy Procedures

The pharmacist and pharmacy technical staff were not blinded. The study statistician provided each site pharmacy with randomization tables. Pharmacists supplied each patient with drug or placebo, both provided by Amgen in separate labeled vials. Pharmacists drew doses in syringes and dispensed them to nursing staff for administration. Drug accountability was monitored by the clinical research organization. Study randomization codes and links to patients were kept in secure records in the pharmacy. All other study personnel involved in administration of drug were blinded.

Randomization and Treatment

The randomization allocation was 1:1 across treatment groups. Each site investigational pharmacist was provided with a unique randomization list using size 4 blocks and prepared study medication, maintaining double blinding. Participants received etanercept (0.8 mg/kg) or a comparable placebo volume subcutaneously shortly after IVIG infusion completion, and then once a week for 2 weeks at the study site within the protocol-specified time windows. All patients received aspirin (80-100 mg/kg per day divided every 6 hours) orally until afebrile, and then the dose was reduced to 3 to 5 mg/kg per day until study end, or longer if needed. Patients continued treatment even if they demonstrated IVIG resistance, for which they received a second IVIG infusion.

Trial Assessments

Participants were monitored for recurrent or persistent fever (>38° C.) after IVIG infusion completion. After discharge, parents recorded temperatures on diaries for review at study visits. Baseline echocardiograms were obtained within 12 hours of IVIG initiation, and then at 2 weeks and 5 to 6 weeks as well as additional testing if clinically indicated. All echocardiograms were reviewed for coronary artery dimensions for the left main coronary artery (LMCA), left anterior descending artery (LAD) and right coronary artery (RCA), as well as for aneurysms. Echocardiographic interpretations and measures were interpreted by blinded core readers at Seattle Children's Hospital, and entered into the database. Laboratory studies were obtained at baseline prior to IVIG, at 1 to 2 days after IVIG, then at 1, 2 and 6 weeks of follow-up. Safety and side-effect profiles were evaluated using reported adverse events following Good Clinical Practice guidelines.

Coronoary Artery (CA) Analyses

Coronary z scores are used clinically to evaluate baseline and change in individual arteries during KD. However, small increments in absolute diameter or body surface area can create large changes in the z scores. Also, the impact and temporal changes on each coronary in KD can differ; therefore, measures of individual coronaries will not provide an accurate estimate of overall treatment response. Furthermore, baseline z scores are linked to ultimate CA dilation. To assess changes in coronary diameters or aneurysm size, 2 different methods were used. Both methods included terms defining CA dilation by z score 0.2.5 consistent with AHA recommendations.

A generalized estimating equation (GEE) model was used to determine z score change values. The GEE model is a standard approach that adjusts for the correlation between observations obtained on the same individual at multiple time points during therapy. A GEE overview is provided at support dot sas dot com. Additionally, the GEE model accounts for interdependence among the 3 measured CAs: left main CA, LAD, and right CA. Because etanercept could have a differing magnitude of impact on change in artery z score depending on baseline diameter, terms for dilation status at baseline and the interaction between baseline dilation and treatment group were included in the model. In a separate analysis, a prespecified algorithm was applied to define overall improvement or worsening based on at least a 20% change in absolute CA dimensions. The results of this classification were assessed by using logistic regression. For consistency, and because no definition of dilation based on absolute measurements is widely used, the same definition was used for dilated (z 0.2.5) for subgroup analyses by algorithm and the GEE.

Statistical Analyses

Sample size calculation was based on the historical initial IVIG resistance rate at Seattle Children's Hospital. Assuming a 17.4% refractory rate in the control group and a 4.3% refractory rate in the etanercept group, 200 participants were required to provide 80% power at a 5% 2-sided type I error rate. The primary efficacy analysis population is a modification of intention-to-treat (mITT), consisting of all randomized participants who received at least 1 study drug dose. The mITT population was analyzed according to randomization assignment. The safety population consists of all participants who received at least 1 study drug dose, based on the treatment actually received. The primary outcome was analyzed based on the Chi-Square test for the mITT population, and the odds of resistance to IVIG calculated using logistic regression with treatment assignment included as a fixed covariate. The t-test for independent samples was used to compare continuous baseline characteristics across treatment groups, and the Chi-square test or Fisher's exact test were used to compare categorical variables. Continuous changes in echocardiographic parameters and lab values were evaluated using the Wilcoxon Rank-Sum test, and overall improvement in coronary artery measurements was assessed using logistic regression. Safety estimates include summaries of serious and non-serious adverse event incidences. All p-values and 95% confidence intervals (CI) are 2-sided, and p<0.05 was used as the criterion for statistical significance. No formal control of Type I error was specified for secondary endpoints, so all analyses beyond the primary hypothesis of difference in IVIG resistant proportion should be interpreted with caution. Analyses were conducted using SAS version 9.4 or R version 3.3.3.

398 eligible participants were approached and 212 were enrolled from May 2009 to April 2016. Eleven were excluded prior to treatment before or after randomization. Two hundred and five participants were randomized to either placebo (102) or etanercept (103) (FIG. 2). Four participants discontinued prior to receiving study medication, leaving a modified intention-to-treat population (mITT) with 100 randomized to etanercept and 101 to placebo. One randomized to etanercept inadvertently received placebo. Most mITT (n=186) participants received IVIG 2 g/kg initiated within 10 days of fever onset. The remaining fifteen participants demonstrated continuing fever and CRP elevation (n=7, etanercept; and n=8, placebo), and IVIG treatment initiated between 10 and 12 days. Demographics including age and gender were well balanced between the treatment groups (Table 4).

TABLE 4

Baseline Demographic Characteristics (mITT Population)

| Charac-teristic | | Etanercept (N = 100) | Placebo (N = 101) | P-value* |
|---|---|---|---|---|
| Age (years) | Mean ± SD | 3.77 ± 2.67 | 3.66 ± 2.75 | 0.765 |
| Age Group | Age ≥1 Year (%) | 85 (85.0%) | 83 (82.2%) | 0.589 |
| | Age <1 Year (%) | 15 (15.0%) | 18 (17.8%) | |
| Gender | Male (%) | 66 (66.0%) | 61 (60.4%) | 0.410 |
| | Female (%) | 34 (34.0%) | 40 (39.6%) | |
| Race Group | Non-Hispanic White (%) | 36 (36.0%) | 43 (42.6%) | 0.880 |
| | African American (%) | 12 (12.0%) | 9 (8.9%) | |

TABLE 4-continued

Baseline Demographic Characteristics (mITT Population)

| Charac-teristic | | Etanercept (N = 100) | Placebo (N = 101) | P-value* |
|---|---|---|---|---|
| | Asian** (%) | 15 (15.0%) | 14 (13.9%) | |
| | Hispanic or Latino# (%) | 19 (19.0%) | 17 (16.8%) | |
| | Other Race (%) | 18 (18.0%) | 18 (17.8%) | |

*P-values from the t-test for continuous variables and the chi-square test for categorical variables;
Hispanic, overwhelmingly Mexican or Central American;
**Asian, overwhelming East Asian, not originating from Indian subcontinent.

(b) Treatment Efficacy

Thirty-five participants (17.4%) in the entire study cohort showed IVIG resistance and received a second IVIG dose according to AHA guidelines. Participants receiving etanercept showed a slightly lower resistance rate (n=13, 13%) than those receiving placebo (n=22, 21.8%), although this difference was not statistically significant (p=0.101, Table 5). The odds ratio comparing etanercept to placebo for the mITT population was 0.54, 95% CI: 0.25-1.14 (FIG. 3).

Results of Chi-Square/Fisher analyses for prespecified subgroups appear in Table 5. No significant treatment differences occurred for gender. Etanercept significantly reduced the IVIG resistance rate (P=0.032) subjects older than 1 year (OR 0.40 95% CI: 0.17 to 0.94), but not in the 33 participants (16%) younger than 1 year (etanercept, n=15; placebo, n=18).

Figure 3:
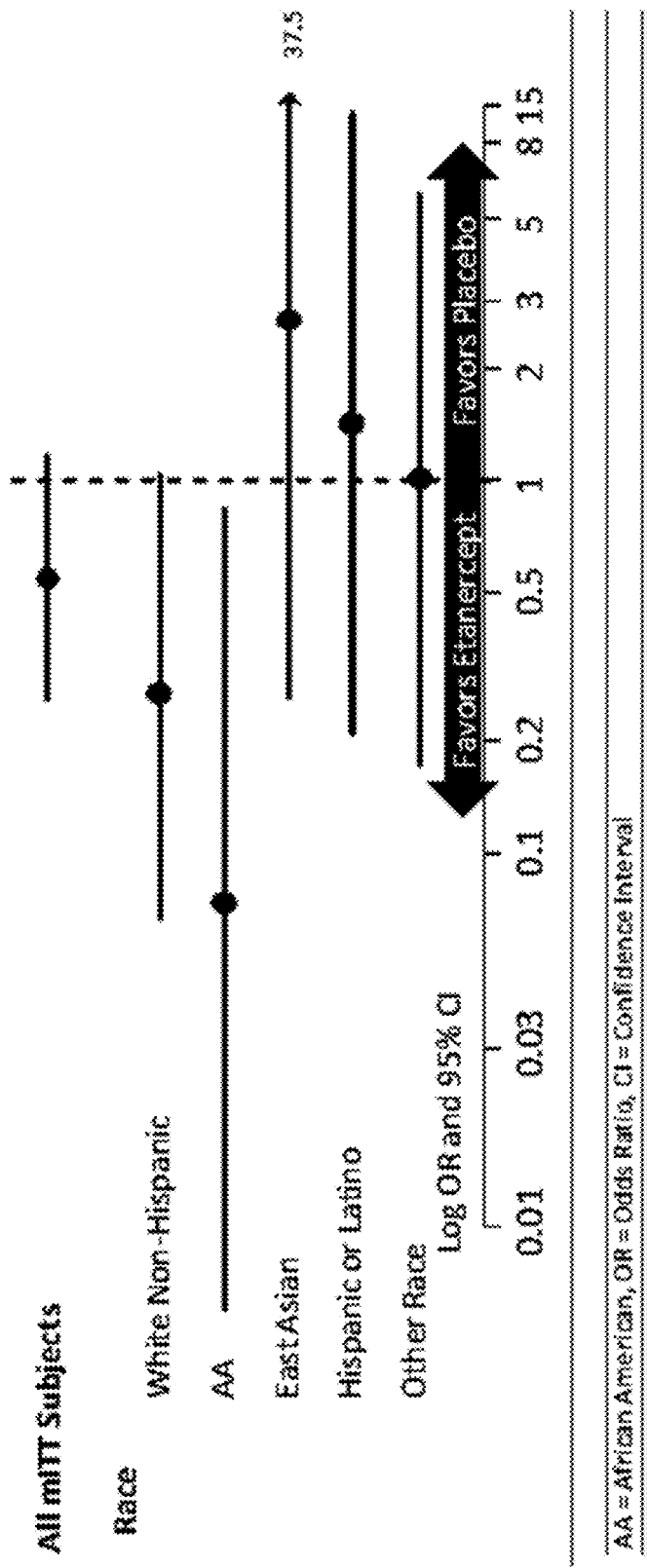
FIG. 3 is a diagram showing primary endpoint-odds ratios and 95% confidence intervals for IVIG resistance in pre-specified ethnic subgroups. A highly favorable response to etanercept was shown for African-American subjects (AA). OR=Odds Ratio; CI=confidence interval.

Variability in fever response to IVIG therapy occurred according to race and ethnicity (Table 5, FIG. 3). Despite a small sample size (n=21), we found that etanercept reduced the refractory rate in AA to 8% (P=0.046, Table 5) (OR: 0.07, 95% CI: 0.01-0.83, FIG. 3). Etanercept also numerically reduced IVIG resistance in WNH, although the difference did not reach statistical significance (OR: 0.26, 95% CI: 0.07-1.04).

TABLE 5

Primary Endpoint - IVIG Response (mITT Population)

| | Etanercept (N = 100) | | Placebo (N = 101) | | |
|---|---|---|---|---|---|
| Subgroup | IVIG-Resistance | Responder | IVIG-Resistance | Responder | P-value* |
| ALL MITT SUBJECTS | 13 (13.0%) | 87 (87.0%) | 22 (21.8%) | 79 (78.2%) | 0.101 |
| AGE GROUP | | | | | |
| Age <1 Year (%) | 4 (26.7%) | 11 (73.3%) | 3 (16.7%) | 15 (83.3%) | 0.674 |
| Age ≥1 Year (%) | 9 (10.6%) | 76 (89.4%) | 19 (22.9%) | 64 (77.1%) | 0.032 |
| GENDER | | | | | |
| Male (%) | 11 (16.7%) | 55 (83.3%) | 16 (26.2%) | 45 (73.8%) | 0.188 |
| Female (%) | 2 (5.9%) | 32 (94.1%) | 6 (15.0%) | 34 (85.0%) | 0.275 |
| RACE GROUP | | | | | |
| Non-Hispanic White (%) | 3 (8.3%) | 33 (91.7%) | 11 (25.6%) | 32 (74.4%) | 0.074 |
| African American (%) | 1 (8.3%) | 11 (91.7%) | 5 (55.6%) | 4 (44.4%) | 0.046 |
| Asian (%) | 3 (20.0%) | 12 (80.0%) | 1 (7.1%) | 13 (92.9%) | 0.598 |
| Hispanic or Latino (%) | 3 (15.8%) | 16 (84.2%) | 2 (11.8%) | 15 (88.2%) | 1.000 |
| Other Race (%) | 3 (16.7%) | 15 (83.3%) | 3 (16.7%) | 15 (83.3%) | 1.000 |

Figure 4:
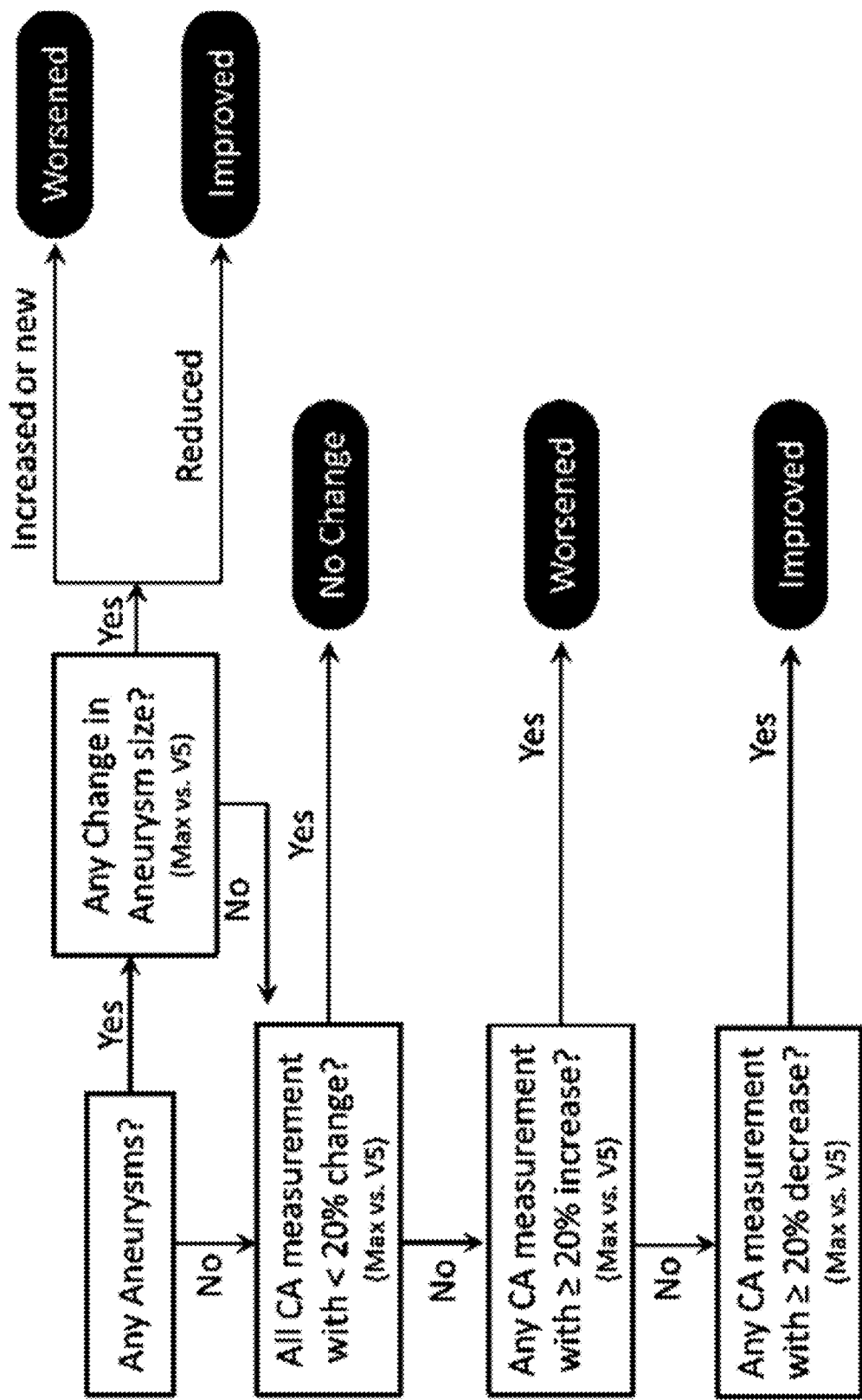
FIG. 4 is a diagram showing an illustrative non-limiting algorithm for determining echocardiographic endpoints during the study.
Figure 5A:
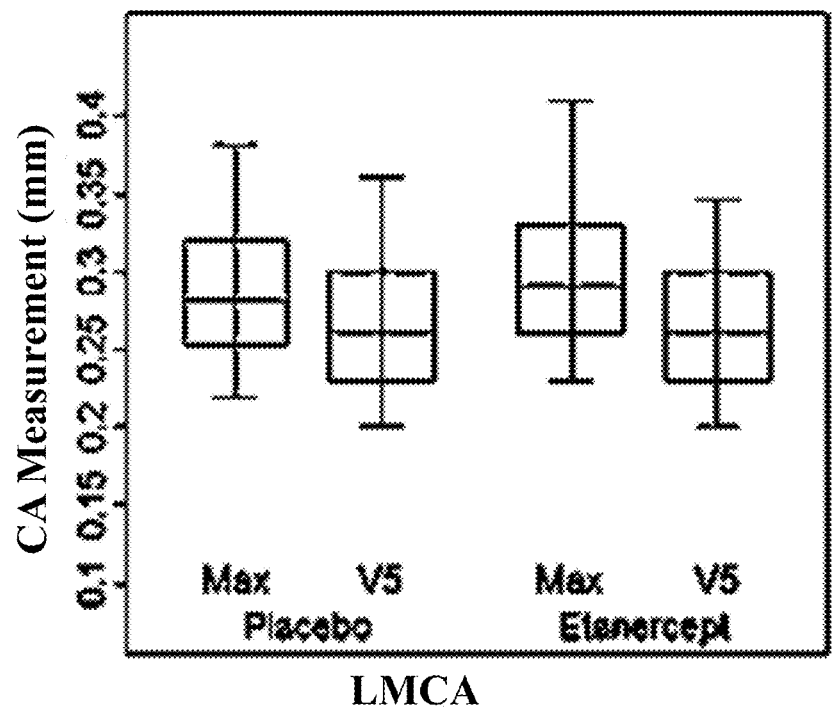
FIGS. 5A-5F are graphs reporting echocardiogram coronary artery measurements after treatment with IVIG and either placebo or etanercept.
Figure 5B:
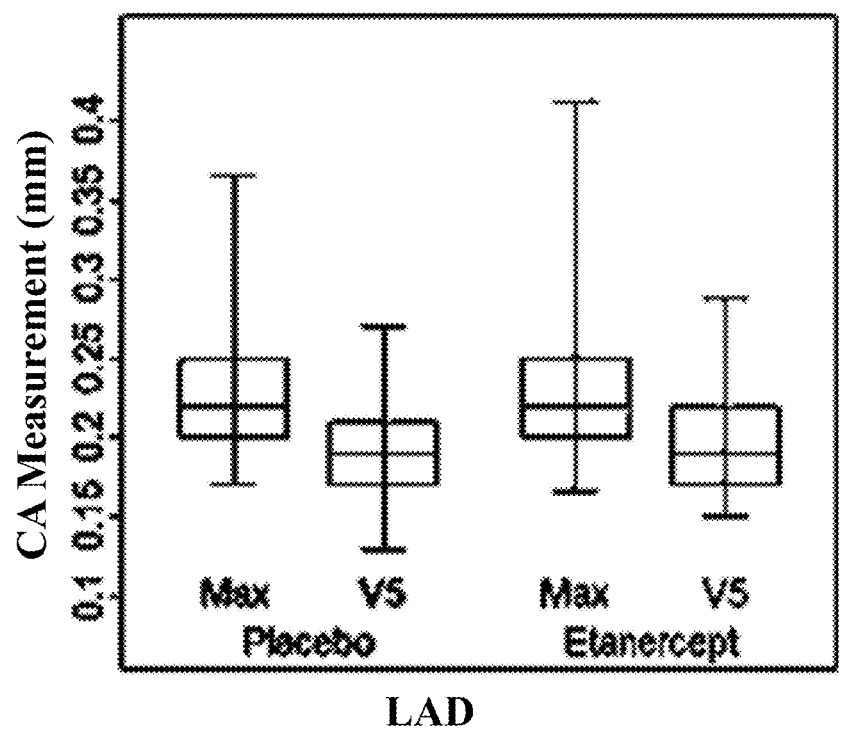
Figure 5C:
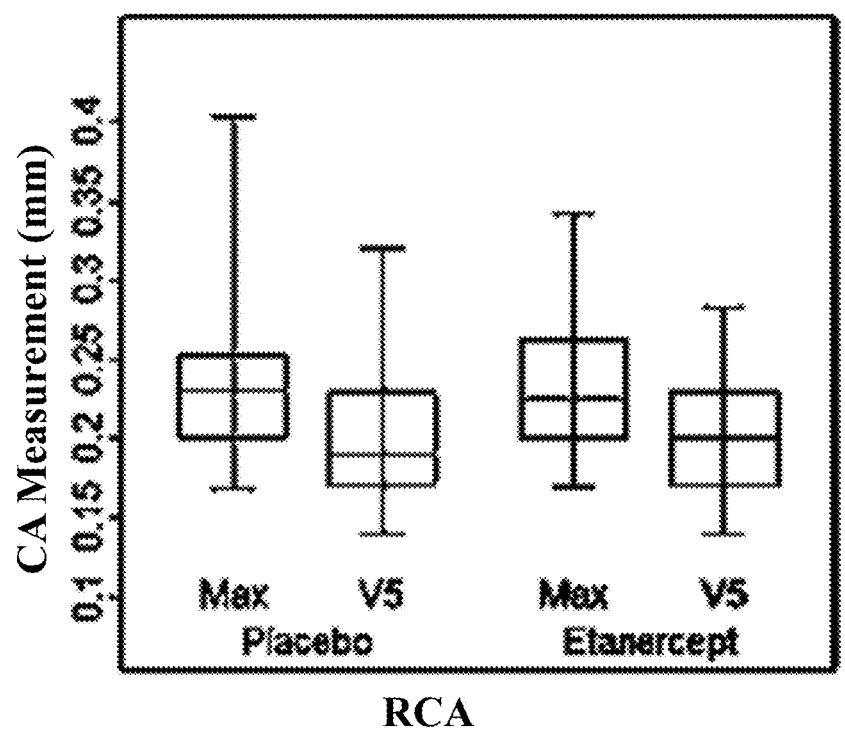
Figure 5D:
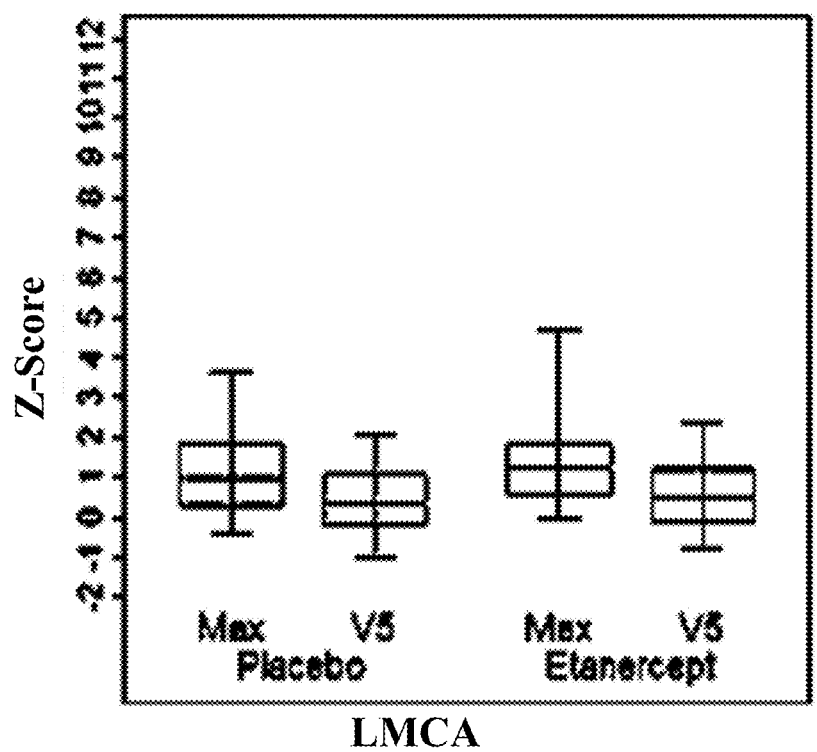
Figure 5E:
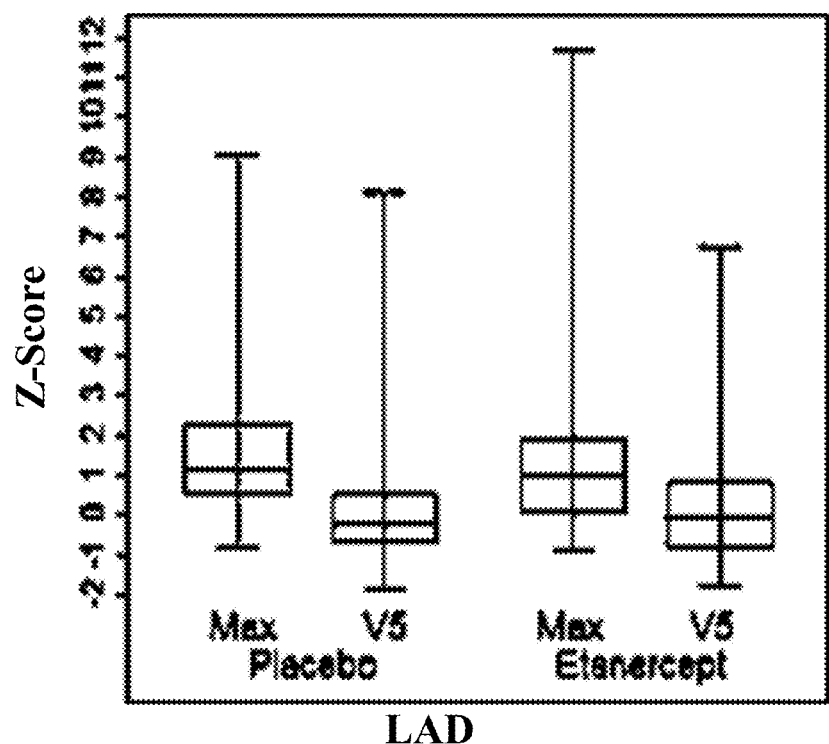
Figure 5F:
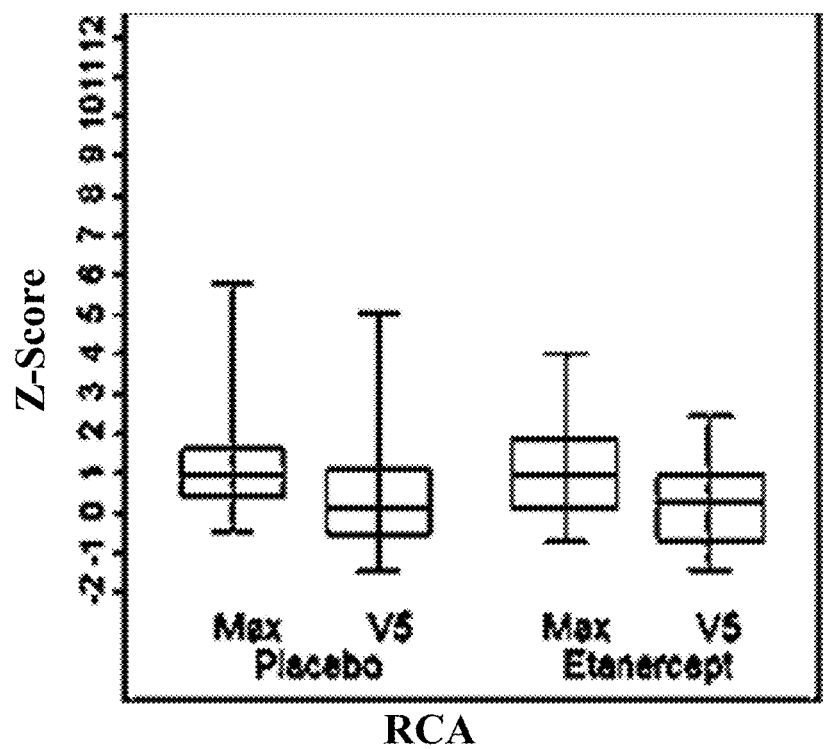
Figure 6B:
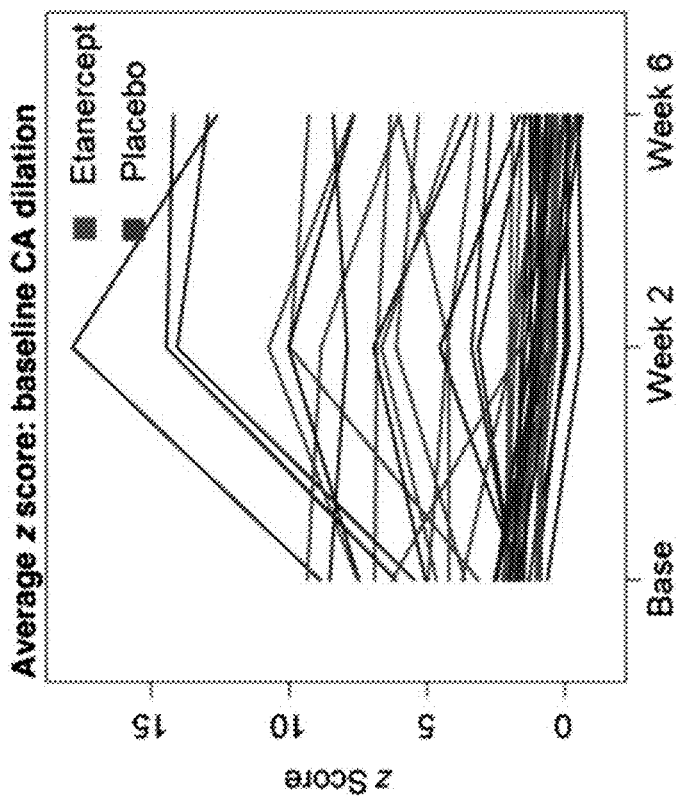
FIGS. 6A-6C show trajectories of the average (mean) of all 3 CA z scores over time in spaghetti diagram format. The center panel indicates more variability in response in placebo subjects with baseline CA dilation (etanercept baseline dilated, n=24; placebo baseline dilated, n=22; etanercept baseline nondilated, n=73; placebo baseline nondilated, n=76). The z scores from individual coronaries were included in the GEE model.
Figure 6A:
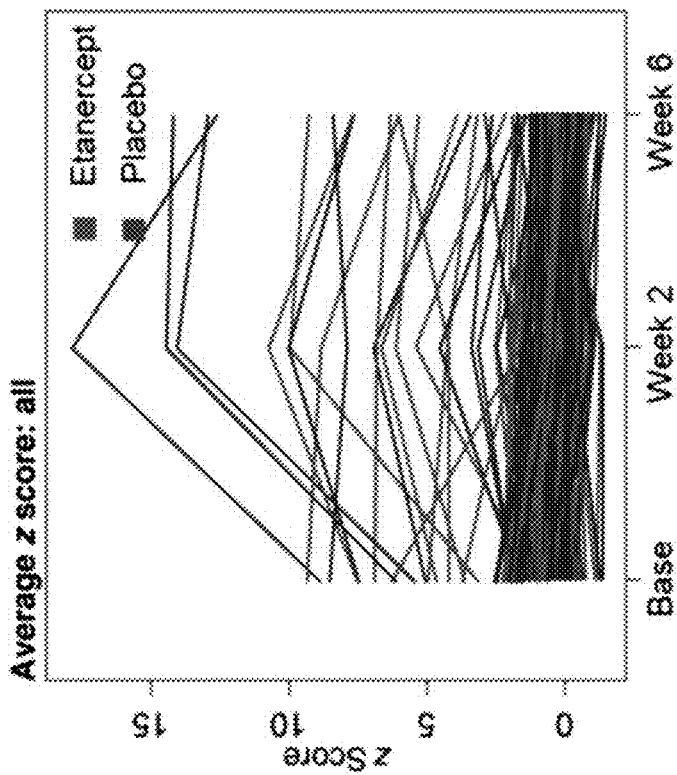
Figure 6D:
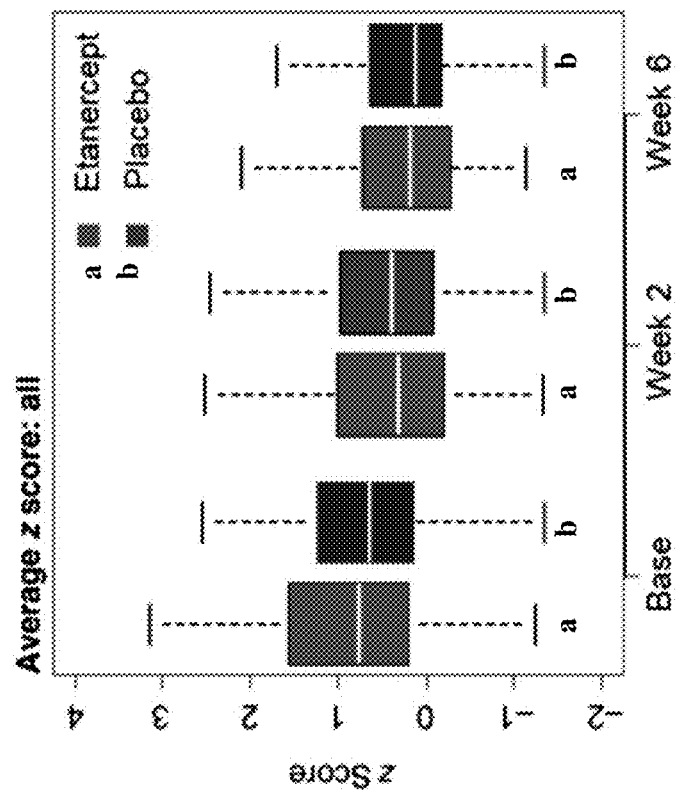
FIGS. 6D-6F shows box plots revealing the 3 CA average z scores overall and within dilation subgroups over time.
Figure 6C:
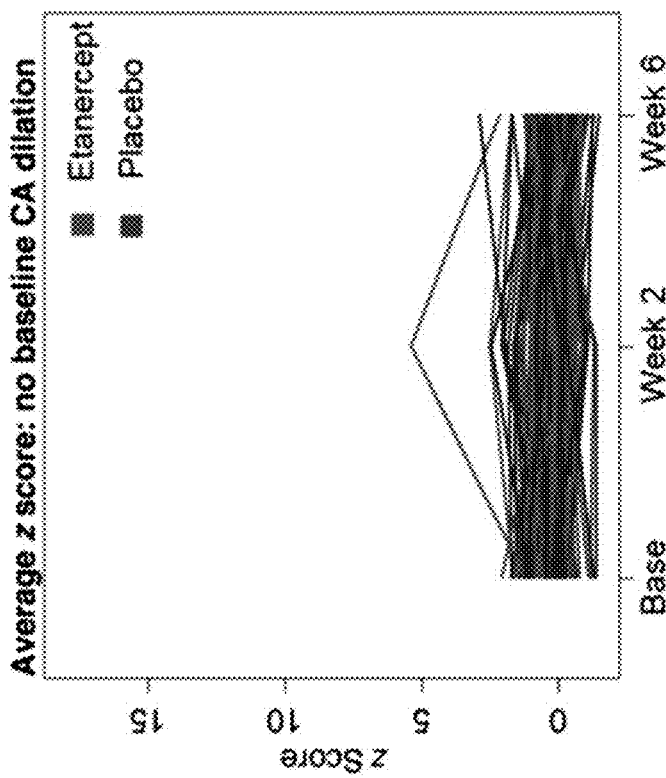
Figure 6E:
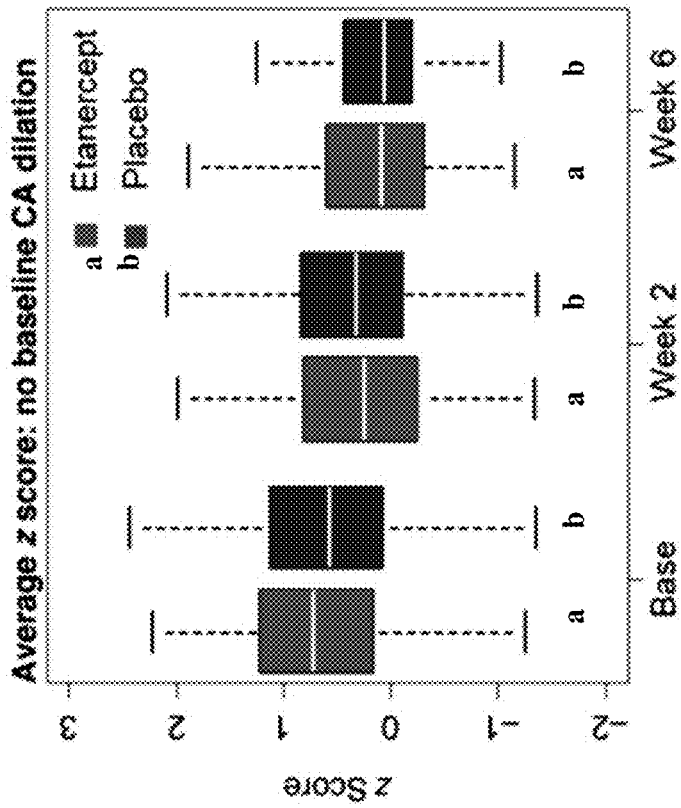
Figure 6F:
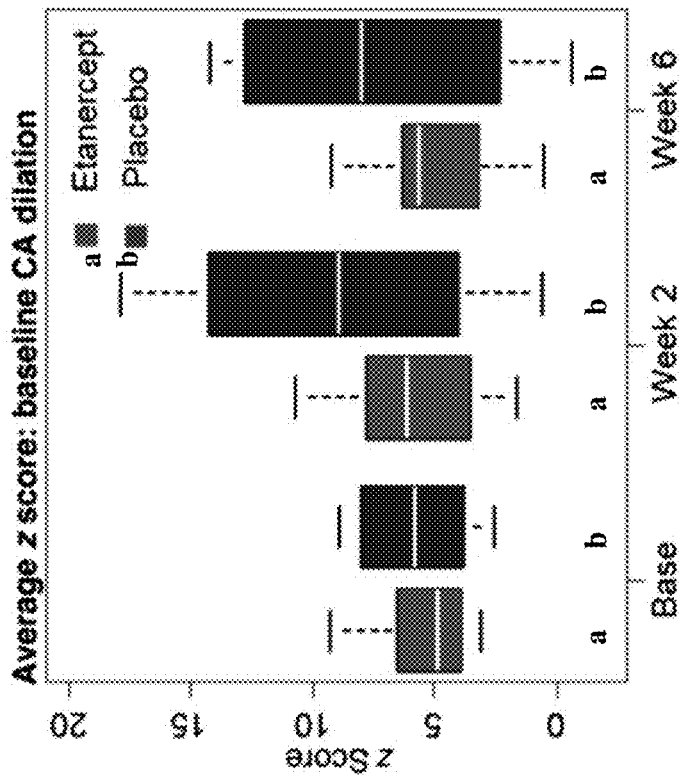

*P-value based on the chi-square test or Fisher's Exact Test as appropriate (c) Coronary Artery Disease by Echocardiography Forty-five mITT participants (22.9%) had at least 1 dilated coronary on the baseline echocardiogram (etanercept n=23; placebo, n=22). The baseline coronary artery dilation rate was similar between the two mITT groups (Table 6). Both placebo and etanercept groups with baseline dilation showed substantially higher rates of coronary dilation defined as an individual z score >2.5 at 6 weeks (36%) than those without initial dilation (4%). Changes in all 3 artery measurements were also considered as described in the FIG. 4, and no significant difference between the placebo and etanercept groups were found (Table 6). Additionally, there were no significant differences in z score changes for the individual coronary arteries in the entire study cohort (FIG. 4). However, among those with CA dilation according at baseline, etanercept reduced the proportion with worsening at the final study visit (p=0.03) (Table 6). FIGS. 6A-6C show trajectories in a spaghetti diagram format for the mean of the 3 coronary z scores at each time point. The diagram reveals a clear dichotomy in the disease course, which depends on presence of early CA dilations. The scatter and range of z score change are substantially greater in the placebo group than in the etanercept group. FIGS. 6D-6F present the data from FIGS. 6A-6C as box plots, revealing cohort median, with 25th and 75th percentiles for the average of the 3 coronary z scores, which illustrate the variation in placebo patients with baseline CA dilation.

Figure 7:
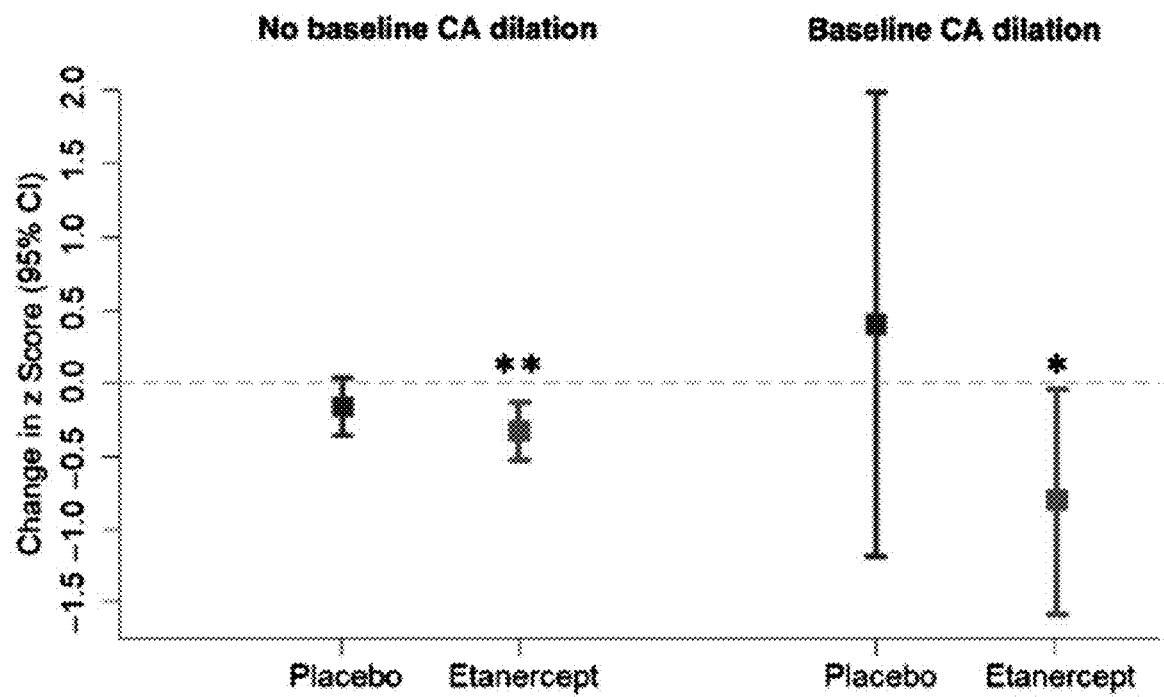
FIG. 7 shows GEE model results for change in z scores over time including all 3 CAs. Etanercept revealed significant reductions in z scores from baseline; the entire 95% CI lies below 0 for patients without and patients with baseline CA dilation. For placebo, there was a numerical reduction among patients with no dilation and a numerical increase among patients with dilation, but neither reached significance. ** P=0.001, * P=0.04.

The GEE model is shown in FIG. 7. Analyses of within-patient change in each treatment group revealed that etanercept subjects experienced significant reductions in z scores across time among those with ($P=0.04$) and without ($P=0.001$) baseline dilation. In contrast, placebo patients showed no significant decrease or increase. The study specific coronary outcome algorithm based on 20% change in absolute diameter (FIG. 4) also indicated that etanercept reduced the proportion with the placebo (8.3% with etanercept; 31.8% with the placebo; $P=0.03$; Table 6) in patients with a dilated coronary at baseline with progressive dilation compared with the placebo (8.3% with etanercept; 31.8% with the placebo; $P=0.03$; Table 6) in patients with a dilated coronary at baseline.

TABLE 6

Coronary Aneurysm Response (mITT Population)

| Change Description | | Etanercept (N = 98)† | Placebo (N = 99)† | P-value |
|---|---|---|---|---|
| Change from Maximum to Week 6 | | | | |
| Coronary Artery Change | Better | 56 (57.1%) | 53 (53.5%) | 0.855 |
| | No Change | 32 (32.7%) | 36 (36.4%) | |
| | Worse | 10 (10.2%) | 10 (10.1%) | |
| Coronary Artery Improvement | Improved | 56 (57.1%) | 53 (53.5%) | 0.611 |
| | Unchanged or Worse | 42 (42.9%) | 46 (46.5%) | |
| Aneurysm Improvement | Improved | 2 (50.0%) | 3 (37.5%) | 1.000 |
| | Unchanged or Worse | 2 (50.0%) | 5 (62.5%) | |
| Change from Baseline to Week 6 | | | | |
| Coronary Artery Change All | Better | 42 (42.9%) | 41 (41.4%) | 0.825 |
| | No Change | 36 (36.7%) | 34 (34.3%) | |
| | Worse | 20 (20.4%) | 24 (24.2%) | |
| Coronary Artery Change CA Dilation | Better | 15 (62.5%) | 14 (63.6%) | 0.030 |
| | No Change | 7 (29.2%) | 1 (4.5%) | |
| | Worse | 2 (8.3%) | 7 (31.8%) | |
| Coronary Artery Change No CA Dilation | Better | 27 (37.0%) | 27 (35.5%) | 0.913 |
| | No Change | 28 (38.4%) | 32 (42.1%) | |
| | Worse | 18 (24.7%) | 17 (22.4%) | |

†Four subjects in the mITT population had no post-baseline echo measurements
‡ CA dilation is defined as a z score ≥2.5 in any artery or any aneurysm at baseline (d) Laboratory Data C-reactive protein (CRP) level serves as a general surrogate for degree of inflammation in KD children. CRP and Hemoglobin were used as index laboratory values. By week 1, 59.8% of placebo and 68.5% of etanercept had normal CRP values (<0.8 mg/dL), though this difference was not significant. Nearly all participants had normal CRP levels by week 6. At week 1, 27.2% of etanercept and 25.8% of placebo participants had normal hemoglobin levels. By 6 weeks, approximately 82% in each group had hemoglobin levels above the lower limit of normal range for age and gender. No significant differences occurred in changes for these values between treatment groups (Table 7).

TABLE 7

Laboratory Changes (mITT Population)*

| Subgroup | | Hemoglobin (g/dL) | | CRP (mg/dL) | |
|---|---|---|---|---|---|
| | | Etanercept | Placebo | Etanercept | Placebo |
| Baseline Value | Median | 10.80 | 10.70 | 7.90 | 8.80 |
| | 25, 75% tile | 9.60, 11.4 | 9.90, 11.2 | 5.02, 15.40 | 6.12, 17.70 |
| Change from Baseline to Week 1 | Median | 0.00 | −0.20 | −7.15 | −8.00 |
| | 25, 75% tile | −1.10, 0.80 | −1.3, 0.70 | −13.69, −4.46 | −16.00, −4.50 |
| Within Normal Range at Week 1 | | 25 (27.2%) | 24 (25.8%) | 63 (68.5%) | 55 (59.8%) |
| Change from Baseline to Week 2 | Median | 0.30 | 0.35 | −7.20 | −8.00 |
| | 25, 75% tile | −0.50, 1.10 | −0.45, 0.90 | −14.75, −4.58 | −17.00, −4.80 |
| Within Normal Range at Week 2 | | 36 (36.4%) | 41 (42.3%) | 80 (85.1%) | 77 (81.9%) |
| Change from Baseline to Week 6 | Median | 1.60 | 1.35 | −7.20 | −7.80 |
| | 25, 75% tile | 0.60, 2.20 | 0.60, 1.90 | −14.60, −4.00 | −14.80, −5.60 |
| Within Normal Range at Week 6 | | 79 (82.3%) | 76 (81.7%) | 90 (94.7%) | 87 (92.6%) |

*No significant differences across treatment groups at any visit (e) Safety

Recurrent fevers at home, necessitating readmission and IVIG retreatment represented all serious adverse events, except for one readmission briefly for influenza in the etanercept arm. Gastrointestinal symptoms were the most common AEs, and there were no differences in the incidence of AEs or SAEs by treatment (Table 8). In particular, infections were uncommon at similar rates with 4 (4.0%) in etanercept and 7 (6.9%) in placebo groups.

TABLE 8

Adverse Events (Safety Population)

|  | Etanercept (N = 99) | Placebo (N = 102) |
| --- | --- | --- |
| Incidence Summary* | | |
| Any adverse event | 53 (53.5%) | 58 (56.9%) |
| Serious adverse event | 9 (9.1%) | 10 (9.8%) |
| Adverse event related to study drug* | 15 (15.2%) | 12 (11.8%) |
| Unexpected adverse event | 22 (22.2%) | 25 (24.5%) |
| Serious unexpected adverse event | 0 (0.0%) | 2 (2.0%) |
| SAE requiring or prolonging hospitalization | 7 (7.1%) | 10 (9.8%) |
| Most Frequent Adverse Events† | | |
| Abdominal Pain | 4 (4.0%) | 3 (2.9%) |
| Anemia | 2 (2.0%) | 5 (4.9%) |
| Arthralgia | 4 (4.0%) | 2 (2.0%) |
| Cough | 5 (5.1%) | 1 (1.0%) |
| Diarrhea | 5 (5.1%) | 1 (1.0%) |
| Emesis | 7 (7.1%) | 7 (6.9%) |
| Epistaxis | 4 (4.0%) | 6 (5.9%) |
| Headache | 6 (6.1%) | 2 (2.0%) |
| Hematoma | 5 (5.1%) | 1 (1.0%) |
| Pyrexia | 13 (13.1%) | 13 (12.7%) |
| Rash | 10 (10.1%) | 12 (11.8%) |
| Urticaria | 2 (2.0%) | 4 (3.9%) |

*Subjects may be counted at most once per row;
†Adverse events in at least 3% of total safety population (f) Study Summary Inability to detect significant improvement in the primary outcome parameter in clinical trials has obstructed progress in treating KD patients. Heterogeneity among KD patients and low background rates of intuitive endpoint targets, such as treatment resistance and persistent coronary artery disease, contribute to this problem. The study reported in Examples 2-6 were designed with IVIG resistance defined by AHA guidelines as the primary endpoint. Fever persistence or recurrence is objective and clearly defined, thereby triggering initiation of rescue therapy.

The study reported herein found that etanercept reduced the overall IVIG resistance rate to 13% compared to 21.8% for placebo. The study accounted for patient heterogeneity through pre-planned subgroup analyses according to demographic parameters: age, gender, race and ethnicity, and baseline coronary artery status. Each characteristic has been well documented to influence either KD susceptibility or treatment response. Although KD is more common in males, no gender differences were found in etanercept effect. Age substantially influences IVIG resistance and coronary artery outcomes (Rosenfeld et al., 1995, J. Pediatrics 126(4):524-529). Patients younger than 1 year show higher risk for developing coronary artery dilation, which further increases for those <6 months. Retrospective North American studies have shown that only 3% of subjects suffering from KD are younger than 6 months, thus rendering this cut-off impractical for stratification. Previous studies have analyzed subgroups by less than or greater than 1 year old, but found no age related effect on corticosteroid response (Newburger, et al., 2007, N Engl J Med. 356(7):663-675).

In contrast, it was found herein that subjects age 1 year and older responded favorably to etanercept with a significant reduction in the IVIG resistance rate. The subject numbers for this age group were fairly large adding to the reliability of this finding.

Kawasaki Disease incidence varies considerably according to race and ethnicity. Very high KD rates occur in Asian populations compared to other races and ethnicities regardless of their geographical location (Holman, et al., 2000, Arch Pediatr Adolesc Med. 154(8):804-808). Additionally, conflicting data exists regarding relative risks for African-American (AA) populations in the U.S. Prior North American prospective clinical trials have documented participant ethnic and racial proportions in their study cohorts. However, no prior study prospectively examined treatment responses according to ethnic and racial characteristics. Under controlled conditions of this study's controlled protocol, a significantly disparate IVIG response in AA individuals was found. The high IVIG resistance rate in AA was a key for detecting a significant etanercept benefit in this subgroup. Without intending to be limited to any particular theory, plausible biological basis for these differences occurs via racial diversity in genotypes, which influence immune regulation and therapeutic response to vaccines, IVIG, and monoclonal antibodies.

The study results showed that pretreatment coronary dilation poses a significant and substantial risk factor for persistent coronary artery abnormality. Unlike pulse methylprednisolone, etanercept significantly reduced progression of coronary artery dilation in this subpopulation. Despite limitations imposed by small sample size, this finding indicates that etanercept provides benefit for patients at high risk for persistent coronary disease. These data are particularly novel considering that published protocols for Japanese trials, indicating clinical benefit in patients receiving corticosteroids, specifically excluded participation of patients with pre-existing coronary abnormalities.

Etanercept reduced IVIG resistance in patients older than 1 year, representing 84% of the total patient population. Additionally, etanercept ameliorated progression of coronary artery dilation in high-risk patients exhibiting dilation or aneurysm at baseline. Further, IVIG resistance varied according to race or ethnicity, and etanercept reduced treatment resistance in higher risk AA subjects. Administration of etanercept was safe and well tolerated in this young population. Thus, the benefit to risk profile appears favorable particularly for select patients.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Enumerated Embodiments

The following exemplary embodiments are provided, the numbering of which is not to be construed as designating levels of importance:

Embodiment 1 provides a method of treating acute Kawasaki Disease (KD) in a human subject in need thereof, the method comprises administering to the subject a therapeutically effective amount of intravenous gamma globulin (IVIG) and a therapeutically effective amount of etanercept.

Embodiment 2 provides the method of embodiment 1, wherein the subject is at least about 2 months old.

Embodiment 3 provides the method of any one of embodiments 1-2, wherein the subject is at least about 12 months old.

Embodiment 4 provides the method of any one of embodiments 1-3, wherein the subject is administered about 0.4 mg/kg to about 2 g/kg IVIG.

Embodiment 5 provides the method of any one of embodiments 1-4, wherein the subject is administered the IVIG over a period of about 10 hours.

Embodiment 6 provides the method of any one of embodiments 1-5, wherein the subject is administered the IVIG intravenously.

Embodiment 7 provides the method of any one of embodiments 1-6, wherein the subject is administered at least one dose of about 0.4 mg/kg to about 1.6 mg/kg etanercept. Embodiment 8 provides the method of any one of embodiments 1-7, wherein the subject is administered at least one dose of about 0.4 mg/kg to about 0.8 mg/kg etanercept.

Embodiment 9 provides the method of any one of embodiments 1-8, wherein administration of the etanercept affords a blood serum steady state concentration of about 600 ng/mL to about 5,000 ng/mL etanercept in the subject.

Embodiment 10 provides the method of any one of embodiments 1-9, wherein the subject is administered the etanercept at least once a week.

Embodiment 11 provides the method of any one of embodiments 1-10, wherein the subject is administered at least three doses of about 0.8 mg/kg etanercept each, wherein the at least three doses are administered about 4 to about 10 days apart from each other.

Embodiment 12 provides the method of any one of embodiments 1-11, wherein the subject is administered the etanercept parenterally.

Embodiment 13 provides the method of any one of embodiments 1-12, wherein the subject is administered the etanercept subcutaneously.

Embodiment 14 provides the method of any one of embodiments 1-13, wherein the etanercept is formulated as part of a pharmaceutical composition further comprising at least one pharmaceutically acceptable carrier.

Embodiment 15 provides the method of any one of embodiments 1-14, wherein the pharmaceutical composition does not comprise a buffer.

Embodiment 16 provides the method of any one of embodiments 1-15, wherein the pharmaceutical composition comprises a buffer.

Embodiment 17 provides the method of any one of embodiments 1-16, wherein the pharmaceutical composition further comprises at least one additional compound selected from the group consisting of benzyl alcohol, mannitol, sorbitol, xylitol, sucrose, lactose, starch, cellulose, gelatin, polyethylene glycol, and tris(hydroxymethyl)aminomethane (tromethamine).

Embodiment 18 provides the method of any one of embodiments 1-17, wherein the pharmaceutical composition comprises etanercept, mannitol, sucrose, tris(hydroxymethyl)aminomethane, and a sterile bacteriostatic aqueous solution comprising benzyl alcohol.

Embodiment 19 provides the method of any one of embodiments 1-18, wherein the pharmaceutical composition comprises etanercept, mannitol, sucrose, tris(hydroxymethyl)aminomethane in a ratio (w:w:w:w) of about 25:40:10:1.25.

Embodiment 20 provides the method of any one of embodiments 1-19, wherein the pharmaceutical composition comprises sterile bacteriostatic water comprising about 0.9% benzyl alcohol.

Embodiment 21 provides the method of any one of embodiments 1-20, wherein the pharmaceutical composition comprises etanercept, citric acid, sodium citrate, sodium chloride, sucrose, and lysine.

Embodiment 22 provides the method of any one of embodiments 1-21, wherein the pharmaceutical composition comprises etanercept, citric acid, sodium citrate, sodium chloride, sucrose, and lysine in a ratio (w:w:w:w) of about 33.3:0.52:9.0:1:6.7:3.1.

Embodiment 23 provides the method of any one of embodiments 1-22, wherein the pharmaceutical composition comprises etanercept, NaCl, L-arginine, sucrose and water.

Embodiment 24 provides the method of any one of embodiments 1-23, wherein the pharmaceutical composition comprises about 50 mg/mL etanercept, about 120 mM NaCl, about 25 mM L-arginine, about 1% (w/v) sucrose, and water.

Embodiment 25 provides the method of any one of embodiments 1-24, wherein the subject is further administered aspirin, salicylic acid, or any salts, esters, or solvates thereof.

Embodiment 26 provides the method of any one of embodiments 1-25, wherein the method treats or prevents fever caused by KD in the subject.

Embodiment 27 provides the method of any one of embodiments 1-26, wherein the method does not cause or trigger any significant adverse event in the subject.

Embodiment 28 provides the method of any one of embodiments 1-27, wherein the method ameliorates progression of coronary artery dilation in high-risk subjects exhibiting dilation or aneurysm before treatment.

Embodiment 29 the method of any one of embodiments 1-28, wherein the method reduces IVIG resistance in the subject.

Embodiment 30 provides the method of any one of embodiments 1-29, wherein the IVIG is administered to the subject before the etanercept.

Embodiment 31 provides the method of any one of embodiments 1-30, wherein the IVIG is administered to the subject after the etanercept.

Embodiment 32 provides the method of any one of embodiments 1-31, wherein the etanercept is administered to the subject at any point during the course of acute KD.

Embodiment 33 provides the method of any one of embodiments 1-32, wherein the subject is African American or non-Hispanic White.

Embodiment 34 provides a method of reducing or preventing IVIG resistance in a subject being administered IVIG for the treatment of KD, the method comprising administering to the subject a therapeutically effective amount of etanercept.

Embodiment 35 provides the method of embodiment 34, wherein the subject is administered at least one dose of about 0.4 mg/kg to about 0.8 mg/kg etanercept.

Embodiment 36 provides the method of any one of embodiments 34-35, wherein the subject is administered the etanercept at least once a week.

Embodiment 37 provides the method of any one of embodiments 34-36, wherein the subject is administered at least three doses of about 0.8 mg/kg etanercept each, wherein the at least three doses are administered about 4 to about 10 days apart from each other.

Embodiment 38 provides the method of any one of embodiments 34-37, wherein the subject is administered the etanercept parenterally.

Embodiment 39 provides the method of any one of embodiments 34-38, wherein the subject is administered the etanercept subcutaneously.

Embodiment 40 provides the method of any one of embodiments 34-39, wherein the subject is African American or non-Hispanic White.

Embodiment 41 provides a method of ameliorating or preventing progression, or promoting regression, of coronary artery dilation in a subject suffering from KD, the method comprising administering to the subject a therapeutically effective amount of etanercept.

Embodiment 42 provides the method of embodiment 41, wherein the subject is being administered IVIG.

Embodiment 43 provides the method of any one of embodiments 41-42, wherein the subject is administered at least one dose of about 0.4 mg/kg to about 0.8 mg/kg etanercept.

Embodiment 44 provides the method of any one of embodiments 41-43, wherein the subject is administered the etanercept at least once a week.

Embodiment 45 provides the method of any one of embodiments 41-44, wherein the subject is administered at least three doses of about 0.8 mg/kg etanercept each, wherein the at least three doses are administered about 4 to about 10 days apart from each other.

Embodiment 46 provides the method of any one of embodiments 41-45, wherein the subject is administered the etanercept parenterally.

Embodiment 47 provides the method of any one of embodiments 41-46, wherein the subject is administered the etanercept subcutaneously.

Embodiment 48 provides the method of any one of embodiments 41-47, wherein the subject is a high-risk subject exhibiting blood vessel dilation or aneurysm.

Embodiment 49 provides the method of any one of embodiments 41-48, wherein the etanercept is administered for about 6 weeks at a weekly dose of from about 0.4 mg/kg to about 1.6 mg/kg.

Embodiment 50 provides the method of any one of embodiments 41-49, wherein the etanercept is administered at a weekly dose of about 0.8 mg/kg.

Embodiment 51 provides the method of any one of embodiments 41-50, wherein the subject has a coronary echocardiogram z-score greater than 2.5.

Embodiment 52 provides the method of any one of embodiments 41-51, wherein the subject is African American or non-Hispanic White.

What is claimed is:

1. A method of treating or ameliorating acute Kawasaki Disease (KD) in a human subject that is aged 12 months or older and that is suffering from acute KD and exhibiting coronary artery dilation or aneurysm,
    wherein the method comprises:
        administering only to the subject that is aged 12 months or older:
            a therapeutically effective amount of intravenous gamma globulin (IVIG), and
            a therapeutically effective amount of a pharmaceutical composition comprising etanercept and at least one pharmaceutically acceptable carrier or excipient;
    wherein the method ameliorates or prevents progression of the coronary artery or aneurysm in the subject.

2. The method of claim 1, wherein the subject is administered about 0.4 mg/kg to about 2 g/kg IVIG.

3. The method of claim 1, wherein the subject is administered the IVIG over a period of about 10 hours.

4. The method of claim 1, wherein the subject is administered the IVIG intravenously.

5. The method of claim 1, wherein the subject is administered at least one dose of about 0.4 mg/kg to about 1.6 mg/kg etanercept.

6. The method of claim 5, wherein the subject is administered at least one dose of about 0.4 mg/kg to about 0.8 mg/kg etanercept.

7. The method of claim 1, wherein administration of the etanercept affords a blood serum steady state concentration of about 600 ng/mL to about 5,000 ng/mL etanercept in the subject.

8. The method of claim 1, wherein the subject is administered the etanercept at least once a week.

9. The method of claim 1, wherein the subject is administered at least three doses of about 0.8 mg/kg etanercept each, wherein the at least three doses are administered about 4 to about 10 days apart from each other.

10. The method of claim 1, wherein the subject is administered the etanercept parenterally.

11. The method of claim 1, wherein the subject is administered the etanercept subcutaneously.

12. The method of claim 1, wherein the pharmaceutical composition does not comprise a buffer.

13. The method of claim 1, wherein the pharmaceutical composition comprises a buffer.

14. The method of claim 1, wherein the pharmaceutical composition further comprises at least one additional compound selected from the group consisting of benzyl alcohol, mannitol, sorbitol, xylitol, sucrose, lactose, starch, cellulose, gelatin, polyethylene glycol, and tris(hydroxymethyl)aminomethane (tromethamine).

15. The method of claim 1, wherein the pharmaceutical composition comprises etanercept, mannitol, sucrose, tris(hydroxymethyl)aminomethane, and a sterile bacteriostatic aqueous solution comprising benzyl alcohol.

16. The method of claim 15, wherein the pharmaceutical composition comprises etanercept, mannitol, sucrose, tris(hydroxymethyl)aminomethane in a ratio (w:w:w:w) of about 25:40:10:1.25.

17. The method of claim 16, wherein the pharmaceutical composition comprises sterile bacteriostatic water comprising about 0.9% benzyl alcohol.

18. The method of claim 1, wherein the pharmaceutical composition comprises etanercept, citric acid, sodium citrate, sodium chloride, sucrose, and lysine.

19. The method of claim 18, wherein the pharmaceutical composition comprises etanercept, citric acid, sodium citrate, sodium chloride, sucrose, and lysine in a ratio (w:w:w:w) of about 33.3:0.52:9.0:1:6.7:3.1.

20. The method of claim 1, wherein the pharmaceutical composition comprises etanercept, NaCl, L-arginine, sucrose and water.

21. The method of claim 20, wherein the pharmaceutical composition comprises about 50 mg/mL etanercept, about 120 mM NaCl, about 25 mM L-arginine, about 1% (w/v) sucrose, and water.

22. The method of claim 1, wherein the subject is further administered aspirin, salicylic acid, or any salts, esters, or solvates thereof.

23. The method of claim 1, wherein the method treats or prevents fever caused by KD in the subject.

24. The method of claim 1, wherein the method does not cause or trigger any significant adverse event in the subject.

25. The method of claim 1, wherein the method reduces IVIG resistance in the subject.

26. The method of claim 1, wherein the IVIG is administered to the subject before the etanercept.

27. The method of claim 1, wherein the IVIG is administered to the subject after the etanercept.

28. The method of claim 1, wherein the etanercept is administered to the subject at any point during the course of acute KD.

29. The method of claim 1, wherein the subject is African American or non-Hispanic White.

30. A method of reducing or preventing IVIG resistance in a subject that is aged 12 months or older and that is suffering from KD and being administered IVIG for the treatment of KD, the method comprising:
administering only to the subject that is aged 12 months or older a therapeutically effective amount of a pharmaceutical composition comprising etanercept and at least one pharmaceutically acceptable carrier or excipient.

31. The method of claim 30, wherein the subject is administered at least one dose of about 0.4 mg/kg to about 0.8 mg/kg etanercept.

32. The method of claim 30, wherein the subject is administered the etanercept at least once a week.

33. The method of claim 30, wherein the subject is administered at least three doses of about 0.8 mg/kg etanercept each, wherein the at least three doses are administered about 4 to about 10 days apart from each other.

34. The method of claim 30, wherein the subject is administered the etanercept subcutaneously.

35. The method of claim 30, wherein the subject is African American or non-Hispanic White.

36. A method of ameliorating progression, preventing progression, or promoting regression of coronary artery dilation in a subject that is aged 12 months or older and that is suffering from KD, the method comprising:
administering only to the subject that is aged 12 months or older a therapeutically effective amount of a pharmaceutical composition comprising etanercept and at least one pharmaceutically acceptable carrier or excipient,
wherein the subject exhibits blood vessel dilation or aneurysm before the administering.

37. The method of claim 36, wherein the subject is being administered IVIG.

38. The method of claim 36, wherein the subject is administered at least one dose of about 0.4 mg/kg to about 0.8 mg/kg etanercept.

39. The method of claim 36, wherein the subject is administered the etanercept at least once a week.

40. The method of claim 36, wherein the subject is administered at least three doses of about 0.8 mg/kg etanercept each, wherein the at least three doses are administered about 4 to about 10 days apart from each other.

41. The method of claim 36, wherein the subject is administered the etanercept subcutaneously.

42. The method of claim 36, wherein the etanercept is administered for about 6 weeks at a weekly dose of from about 0.4 mg/kg to about 1.6 mg/kg.

43. The method of claim 36, wherein the etanercept is administered at a weekly dose of about 0.8 mg/kg.

44. The method of claim 36, wherein the subject has a coronary echocardiogram z-score greater than 2.5.

45. The method of claim 36, wherein the subject is African American or non-Hispanic White.

46. A method of ameliorating progression, preventing progression, or promoting regression of coronary artery dilation in a subject that is aged 12 months or older and that is suffering from KD, the method comprising:
administering only to the subject that is aged 12 months or older a therapeutically effective amount of a pharmaceutical composition comprising etanercept and at least one pharmaceutically acceptable carrier or excipient,
wherein the subject has a coronary echocardiogram z-score greater than 2.5 before the administering.

47. The method of claim 46, wherein the subject is being administered IVIG.

48. The method of claim 46, wherein the subject is administered at least one dose of about 0.4 mg/kg to about 0.8 mg/kg etanercept.

49. The method of claim 46, wherein the subject is administered the etanercept at least once a week.

50. The method of claim 46, wherein the subject is administered at least three doses of about 0.8 mg/kg etanercept each, wherein the at least three doses are administered about 4 to about 10 days apart from each other.

51. The method of claim 46, wherein the subject is administered the etanercept subcutaneously.

52. The method of claim 46, wherein the etanercept is administered for about 6 weeks at a weekly dose of from about 0.4 mg/kg to about 1.6 mg/kg.

53. The method of claim 46, wherein the etanercept is administered at a weekly dose of about 0.8 mg/kg.

54. The method of claim 46, wherein the subject is African American or non-Hispanic White.

55. A method of reducing or preventing IVIG resistance in an African American subject that is aged 12 months or older and is suffering from KD and being administered IVIG for the treatment of KD, the method comprising:

administering only to the subject that is aged 12 months or older a therapeutically effective amount of a pharmaceutical composition comprising etanercept and at least one pharmaceutically acceptable carrier or excipient.

56. The method of claim 55, wherein the subject is administered at least one dose of about 0.4 mg/kg to about 0.8 mg/kg etanercept.

57. The method of claim 55, wherein the subject is administered the etanercept at least once a week.

58. The method of claim 55, wherein the subject is administered at least three doses of about 0.8 mg/kg etanercept each, wherein the at least three doses are administered about 4 to about 10 days apart from each other.

59. The method of claim 55, wherein the subject is administered the etanercept subcutaneously.

* * * * *